(12) United States Patent
Kuenzi et al.

(10) Patent No.: US 11,617,532 B2
(45) Date of Patent: Apr. 4, 2023

(54) ASSEMBLY OF HARNESS AND SENSOR SUBSTRATE PLATES

(71) Applicant: Sentier HC LLC, Milwaukee, WI (US)

(72) Inventors: Rodney Kuenzi, Waukesha, WI (US); Robert L. Young, Waukesha, WI (US); William Merrick, Milwaukee, WI (US); James Stuart Saunders, Chicago, IL (US); Keith Jasinski, Milwaukee, WI (US); Schon A. Gross, Ashburn, VA (US)

( * ) Notice: Subject to any disclaimer, the term of this patent is extended or adjusted under 35 U.S.C. 154(b) by 773 days.

(21) Appl. No.: 16/481,885

(22) PCT Filed: Feb. 5, 2018

(86) PCT No.: PCT/US2018/016800
§ 371 (c)(1),
(2) Date: Jul. 30, 2019

(87) PCT Pub. No.: WO2018/144972
PCT Pub. Date: Aug. 9, 2018

(65) Prior Publication Data
US 2019/0374122 A1 Dec. 12, 2019

Related U.S. Application Data

(60) Provisional application No. 62/558,227, filed on Sep. 13, 2017, provisional application No. 62/454,275, (Continued)

(51) Int. Cl.
*A61B 5/00* (2006.01)
*A61B 5/318* (2021.01)
(Continued)

(52) U.S. Cl.
CPC ............ *A61B 5/318* (2021.01); *A01K 27/002* (2013.01); *A01K 29/005* (2013.01);
(Continued)

(58) Field of Classification Search
CPC .. A01K 27/002; A01K 29/005; A61B 5/0024; A61B 5/6831
See application file for complete search history.

(56) References Cited

U.S. PATENT DOCUMENTS 5,289,822 A 3/1994 Highe et al.
5,353,793 A 10/1994 Bornn
(Continued)

FOREIGN PATENT DOCUMENTS

| KR | 20180063625 | * | 6/2018 | ............. A61B 5/024 |
| KR | 20180063685 | * | 6/2018 | ........... A01K 27/002 |
| WO | WO 2015170186 | * | 11/2015 | ............. G08B 21/12 |

*Primary Examiner* — Hongmin Fan
(74) *Attorney, Agent, or Firm* — Joel Skinner; Skinner and Associates

(57) ABSTRACT

Assembly of harness and sensor substrate plates for monitoring vital signals of a patient is provided. More specifically, the present invention provides a harness, a sensor substrate plate, and related devices for non-invasively monitoring vital signals of a patient. The sensor substrate plate provides removable attachment to the skin of a patient to measure vital signals of the patient. The sensor substrate plate comprises an elongated main body comprising an upper surface and an under surface. The upper surface is configured to removably contact the skin surface of the patient. Further, a plurality of slots on the upper surface of the main body is mechanically and electrically configured to hold sensors or electrodes for monitoring biometric parameters of the patient. The upper surface also includes a first through hole mechanically and electrically configured to hold an electrical connector; and a first end and a second end of the main body.

2 Claims, 33 Drawing Sheets

Related U.S. Application Data filed on Feb. 3, 2017, provisional application No. 62/454,279, filed on Feb. 3, 2017.

(51) Int. Cl.
| | | |
|---|---|---|
| *A61F 13/42* | (2006.01) | |
| *A01K 27/00* | (2006.01) | |
| *A01K 29/00* | (2006.01) | |
| *A61B 5/026* | (2006.01) | |
| *A61B 5/251* | (2021.01) | |

(52) U.S. Cl.
CPC .......... *A61B 5/0006* (2013.01); *A61B 5/0024* (2013.01); *A61B 5/6831* (2013.01); *A61F 13/42* (2013.01); *A61B 5/0263* (2013.01); *A61B 5/251* (2021.01); *A61B 2503/40* (2013.01); *A61B 2560/0468* (2013.01); *A61B 2562/16* (2013.01); *A61F 2013/424* (2013.01); *H01M 2220/30* (2013.01); *Y02E 60/10* (2013.01)

(56) References Cited

U.S. PATENT DOCUMENTS

| | | | |
|---|---|---|---|
| 2010/0212269 A1* | 8/2010 | Dell'Agnese | A01K 27/006 |
| | | | 119/858 |
| 2012/0029309 A1 | 2/2012 | Pacquet et al. | |
| 2017/0006834 A1* | 1/2017 | Waters | A01K 27/002 |
| 2018/0110672 A1* | 4/2018 | Kasravi | A01K 27/008 |

\* cited by examiner

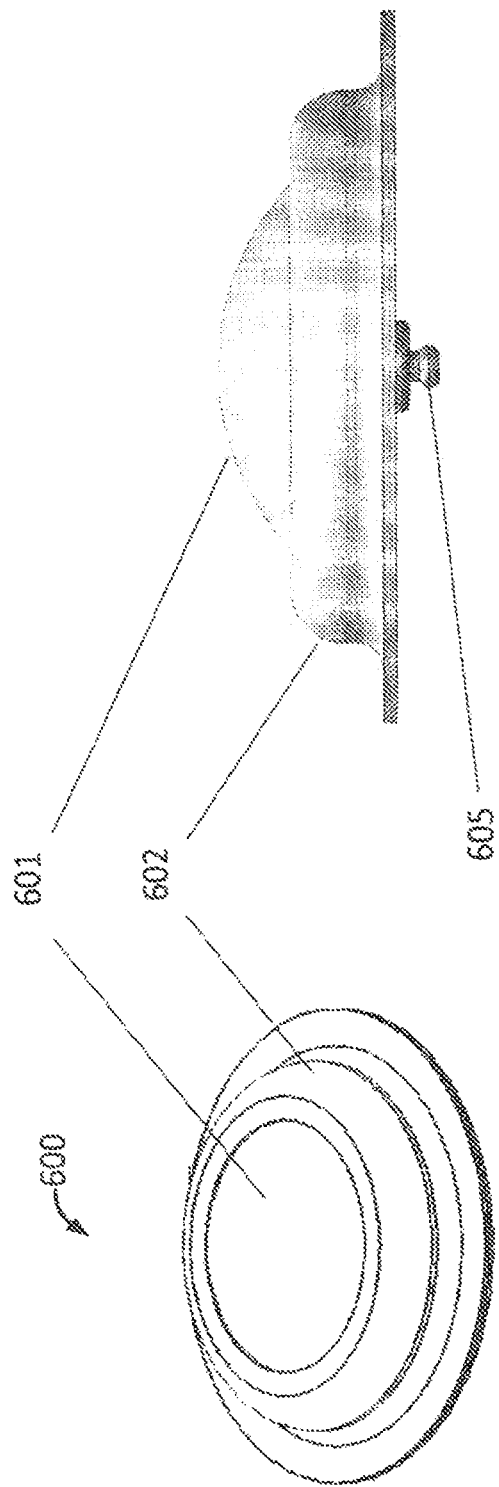
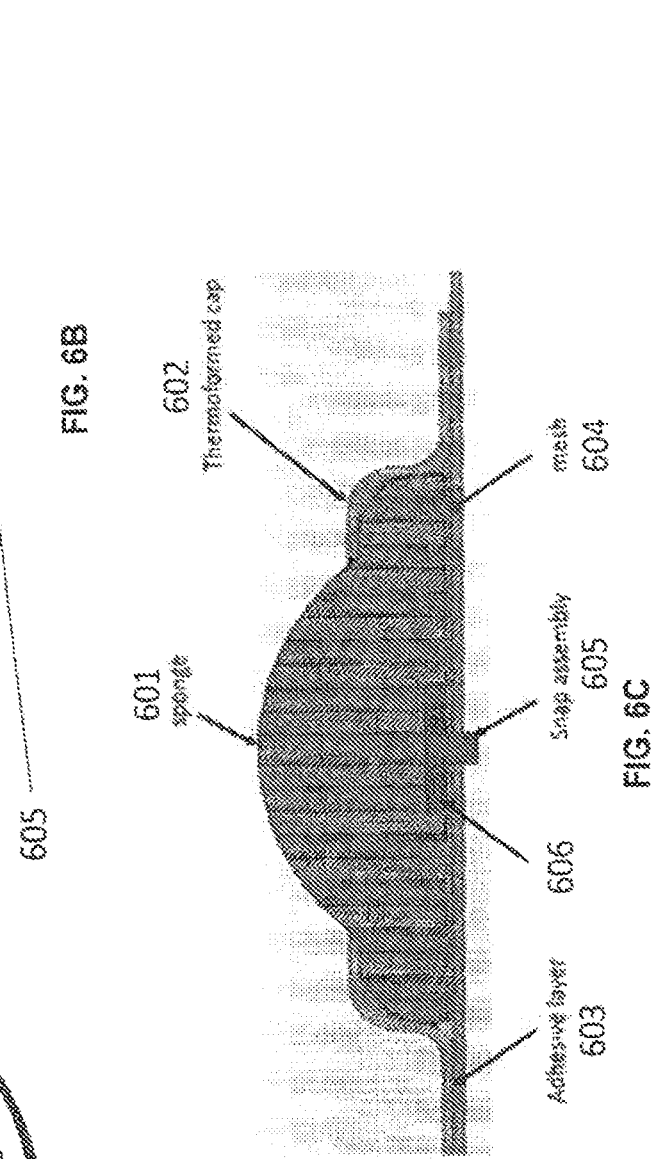

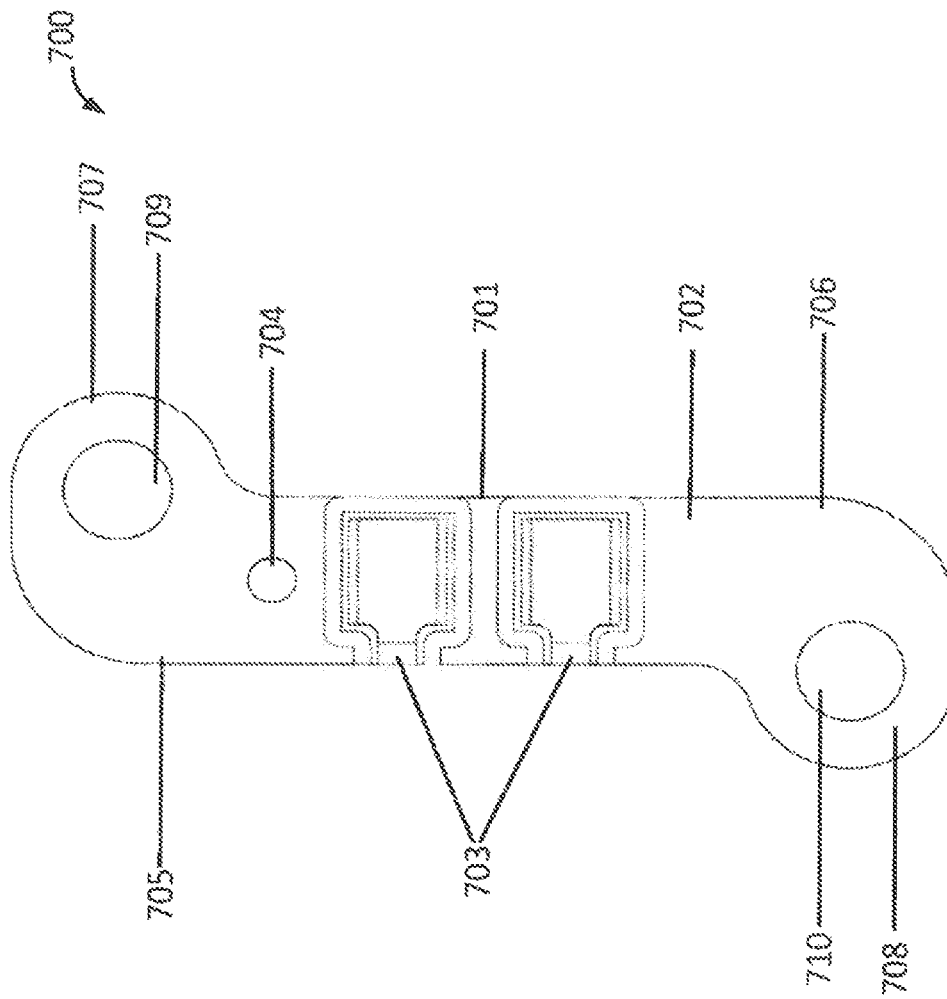

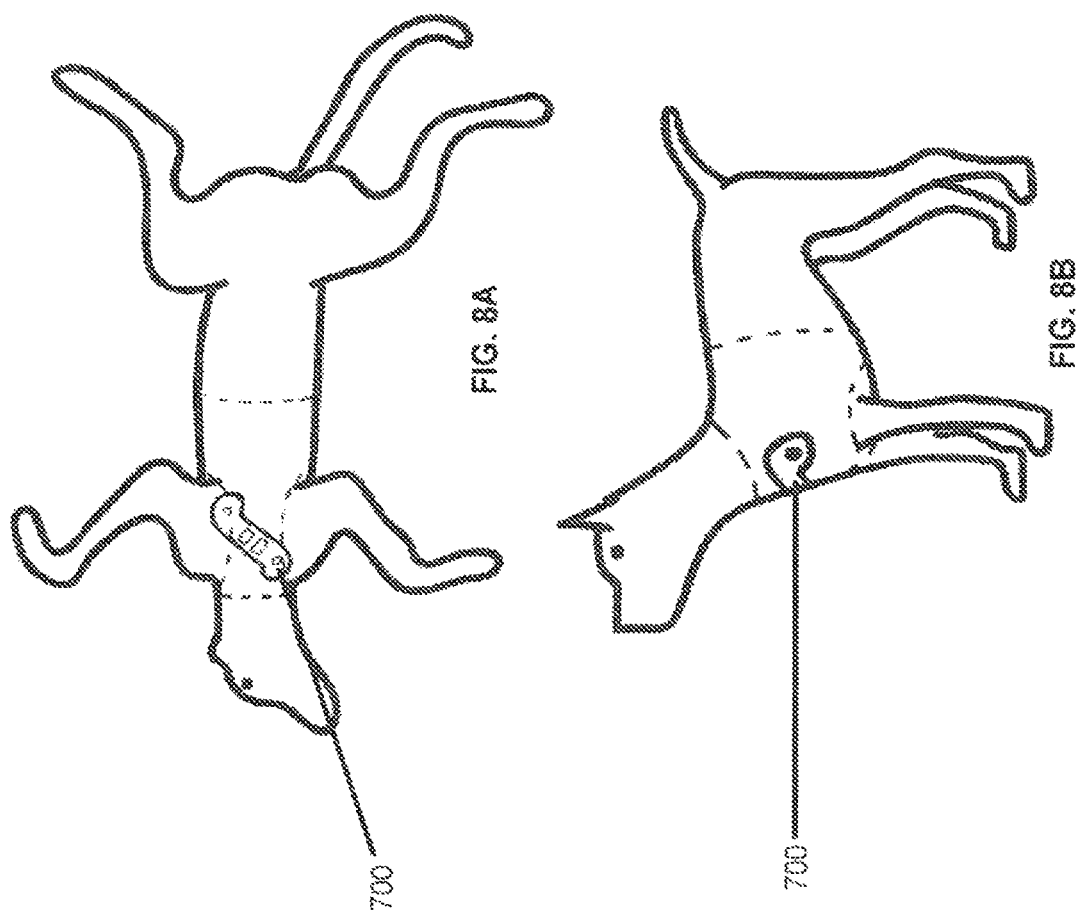

| # | Part | Description | Quantity |
|---|------|-------------|----------|
| 1 | | SensorPad2mm<br>Dimensions: 1.7 x 3.9 x 0.2 inch<br>Volume: 0.2 inch³<br>Material: Tango Grey<br>Paint Level: n/a<br>Finish Level: 1 | 1 |

FIG. 10A

| # | Part | Description | Quantity |
|---|------|-------------|----------|
| 2 | | SensorPad1.2mm<br>Dimensions: 1.7 x 3.9 x 0.1 inch<br>Volume: 0.2 inch³<br>Material: Somos 8120<br>Paint Level: n/a<br>Finish Level: 1 | 1 |

FIG. 10B

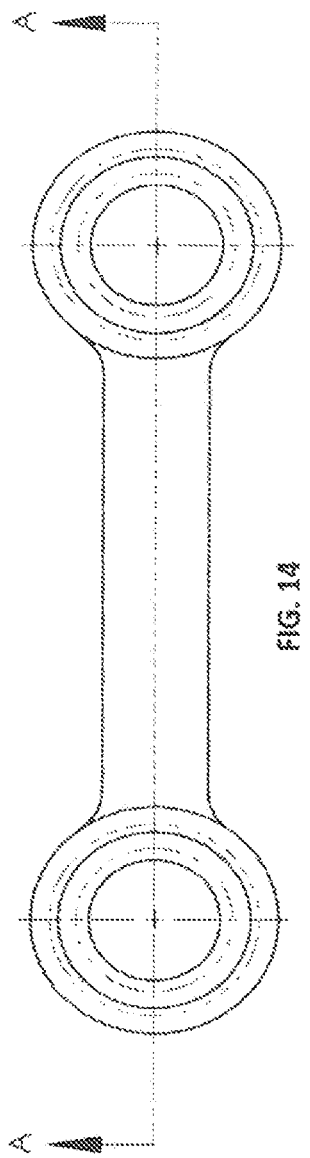
FIG. 14
FIG. 15
SECTION A-A
FIG. 16

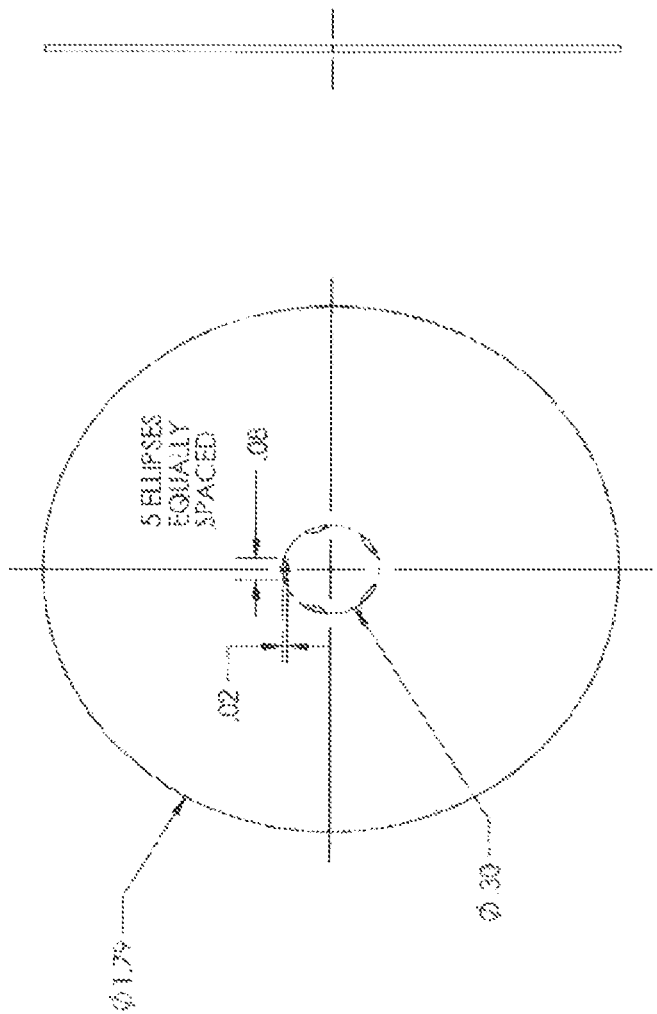

FIG. 26
FIG. 28
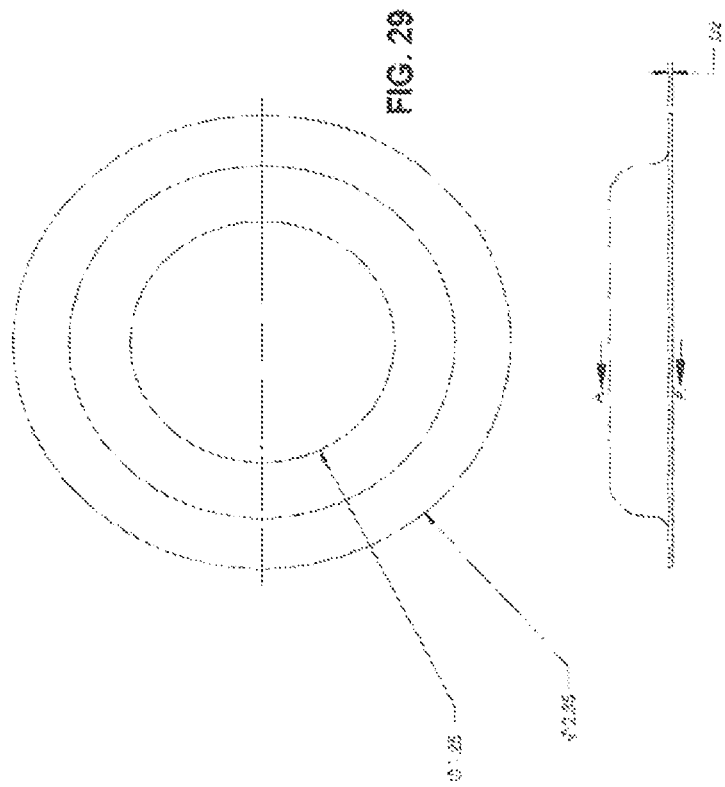
FIG. 29
FIG. 27

OPEN RING PRONG NO SEW SNAP FASTENER
SIZE 16 (11 mm)

ASSEMBLY OF HARNESS AND SENSOR SUBSTRATE PLATES

CROSS-REFERENCE TO RELATED APPLICATIONS

This application claims priority from U.S. Provisional Application 62/454,275, entitled "SENSOR SUBSTRATE PLATES," filed Feb. 3, 2017, U.S. Provisional Application 62/454,279, entitled "HARNESS FOR NON-INVASIVE MONITORING OF ANIMALS," filed Feb. 3, 2017, and U.S. Provisional Application 62/558,227, entitled "SENSOR SUBSTRATE PLATES," filed Sep. 13, 2017, all of which are hereby incorporated by reference in their entirety for all purposes.

BACKGROUND OF THE INVENTION

In one aspect, the field of the invention relates to a harness for one or more veterinary sensor substrate plates and related devices for non-invasive patient monitoring. More particularly, the invention relates to sensor substrate plates and ECG electrodes (e.g., wet ECG electrodes) for the non-invasive use of biometric probes and electrodes on monitoring vital signals of a patient. In another aspect, the field of the invention relates to electrodes, especially wet electrodes without the need of hair removal for non-invasive patient monitoring.

In many veterinary practices, measuring and monitoring a physiological state or condition of an animal may be necessary. In particular, non-invasive monitoring may be desired in medical and surgical veterinary practices for ease in measuring the physiological and biological system of the animal. For example, it is often desirable to monitor and record an electrocardiograph, a $SpO_2$ level, a glucose level, a temperature, and/or any other vital sign of an animal. As mentioned, said measurements help determine the physiological state of an animal and may provide necessary data in determining if the animal may require veterinary care. Alternatively, the data may be used during animal testing, in which case the measurements and/or data may be used to observe changes in the biological condition of a test subject.

Electronic sensors are one way to measure and monitor physiological conditions of an animal. In some instances, electronic sensors may be connected to a monitoring device that processes and stores data acquired from the electronic sensors. In order to connect the aforementioned sensors to the monitoring device, wiring may be required. However, the use of wired data acquisition systems may either require an animal to be incapacitated or hindered in order to allow for accurate measurements. Further, if the animal is allowed to move during data acquisition, it may compromise the data readings. In addition, the wiring and the sensor may be pulled or disconnected from the animal during normal use, resulting in incorrect or inaccurate data measurements.

Further, in order to function properly and provide accurate results, many electronic sensors require a close adherence to the animal. For example, during an electrocardiogram the electronic sensors may require skin contact and, therefore, a portion of the animal may be required to be shaven to provide an adequate surface for the electronic sensor to be applied thereto. Further, there is a need for a harness or apparatus for use in monitoring the physiological conditions of an animal that overcomes the drawbacks of wired data acquisition technology. Further, there is a need for a harness or apparatus that fits the size and shape of the animal it is applied thereto to allow an electronic sensor to be in the necessary proximity and have the required adherence to a surface of an animal to provide accurate measurements from the sensor.

Further, there are many limitations for currently available sensor substrates or related devices as they either allow one to only invasively monitor vital signals of a patient or allow one to only monitor one specific vital signal of a patient. For example, U.S. Pat. No. 5,743,261 describes methods and apparatus for the invasive use of oximeter probes. U.S. Pat. No. 5,715,816 disclosed oximeter probes and methods for the invasive use thereof. U.S. Pat. No. 5,429,129 described an apparatus for determining spectral absorption by a specific substance in a fluid. U.S. Pat. No. 5,417,207 disclosed an apparatus for the invasive use of oximeter probes. U.S. Pat. Nos. 5,368,025 and 5,217,012 disclosed non-invasive oximeter probes. U.S. Pat. No. 6,322,518 described method and apparatus for measuring cardiac output. U.S. Pat. No. 6,266,549 disclosed apparatuses and methods for evaluating cardiac functions. U.S. Pat. No. 6,438,400 disclosed electrodes for evaluating cardiac functions via esophagus. None of these patents disclose sensor substrate plates and/or ECG electrodes (e.g., wet ECG electrodes) capable of non-invasively monitoring multiple vital signals of a patient at the same time and through the same sensor substrate plate.

Therefore, there is a need for a wet electrode that does not require hair to be removed from the animal for use thereof. Further, there is a need for an animal friendly sensor substrate plate and/or an electrode (e.g., a wet ECG electrode) which would allow one to monitor the vital signals and the physiological conditions of an animal without requiring shaving skin surface of the animal. Further, needed in the art are sensor substrate plates and/or ECG electrodes (e.g., wet ECG electrodes) that allow one to simultaneously and non-invasively monitor multiple vital signals of a patient especially for a non-human patient, such as companion animals, primates, lab animals, pocket pets and reptiles.

SUMMARY OF THE INVENTION

In one aspect, some embodiments of the invention provide a harness for use on an animal, the harness comprising a bottom portion with a front edge, a rear edge, and a pocket and a top portion with a front edge, a rear edge, and an aperture. Further, the harness includes side portions extending from each side of the bottom portion, side portions extending from each side of the top portion, and mating connectors on the side portions allowing the side portions of the bottom portion to be connected to the side portions of the top portion. In this embodiment, a sensor is positioned within the pocket and the side portions of the bottom portion and the side portions of the top portion are connected to form a first and a second aperture for a front legs of the animal. Additionally, the harness is configured to a size and a shape of the animal.

In this particular embodiment the matting connectors may comprise of a set of hooks located on the side portions of the bottom portion and a set of straps located on the side portions of the top portion, whereby the set of straps insert and loop around the set of hooks. In particular, the harness further comprises a case releasably attached to the top portion by a set of hook and loop tabs. Further, a monitoring device may be inserted into the case and connected to the sensor using a set of wires. The aforementioned aperture provides a path for connecting the sensor and the monitoring device with the set of wires. The sensor and monitoring device may be used to monitor and/or record a physiological measurement of the animal including an electrocardiogram, an electrocardiograph, an oxygen saturation measurement, a heart rate, a temperature, a glucose level, a velocity, an acceleration, or the like. Specifically, the harness is to be used on a non-human animal.

Some embodiments of the invention provide an apparatus for monitoring an animal comprising a harness to be worn by the animal that is configured to a size and a shape of the animal and comprises an aperture and a pocket and an at least one sensor for recording a physiological measurement of the animal including an at least one wire extending therefrom. Further, the sensor is placed within the pocket and the aperture provides a path for the wire to pass therethrough. Additionally, the animal is preferably a non-human animal and the apparatus further includes a monitoring device releasably attached to the harness and connected to the sensor by the at least one wire. The physiological measurement may include an electrocardiogram, an electrocardiograph, an oxygen saturation measurement, a heart rate, a temperature, a glucose level, a velocity, an acceleration, or the like.

In another aspect, the application discloses an electrode, such as a wet electrode. The wet electrode of the application does not require hair removal of the subject's skin before its application. In one embodiment, the wet electrode is a wet ECG electrode such as a wet gel ECG electrode.

In one embodiment, the wet electrode can be used independently, separately from any sensor substrate plate. In one embodiment, the wet electrode can be used with a sensor substrate plate.

In one embodiment, a sensor substrate plate and/or an electrode such as an ECG electrode (e.g., a wet gel ECG electrode) for non-invasively monitoring vital signals of a patient is provided. More specifically, in this embodiment, a sensor substrate plate and device and/or an electrode such as an ECG electrode (e.g., a wet gel ECG electrode) for non-invasively and simultaneously monitoring vital signal of multiple tissues of a patient by applying multiple electrodes, transducers or sensors to multiple skin locations of the patient and measuring a resulting electrical or photo-electric characteristic induced in the locations of the patient is provided. The wet electrode, such as a wet ECG electrode (e.g., a wet gel ECG electrode), may be used either in combination with the sensor substrate plate or independently.

One embodiment provides an electrode, such as an ECG electrode (e.g., a wet ECG electrode), for monitoring a patient. In some embodiments, the electrode, such as an ECG electrode, may be used in combination with a sensor substrate plate as discussed herein. In other embodiments, the electrode, such as an ECG electrode, may be used independently from any sensor substrate. For example, the electrode (e.g., the wet gel ECG electrode) may be used directly on a patient without the need of a sensor substrate.

In another aspect, an electrode, such as a wet electrode and/or a sensor substrate plate, for removable attachment to the skin of a patient to measure vital signals of the patient is provided. In one embodiment, the wet electrode includes a conductive liquid that is directly and/or removably applied to the skin of a patient without the need of hair removal of the skin to measure vital signals of the patient. In another embodiment, the wet electrode comprises a conductive liquid that is combined with a substrate, such as a sensor substrate plate, before its application to the skin of a subject.

In one embodiment, the sensor substrate plate may include an elongated main body comprising an upper surface and an under surface, wherein the upper surface is configured to removably contact the skin surface of the patient, a plurality of slots on the upper surface of the main body that are mechanically and electrically configured to hold sensors or electrodes for monitoring biometric parameters of the patient, a first through hole mechanically configured to hold an electrical connector, and a first end and a second end of the main body.

The sensor substrate plate further includes a first end portion that is integrated to the first end of the main body, the first end portion comprising a second through hole configured to hold a first electrode; and a second end portion that is integrated to the second end of the main body, the second end portion comprising a third through hole mechanically and electrically configured to hold a second electrode. The sensor substrate plate may allow the first electrode and the second electrode to monitor biometric parameters of two different tissues of the patient.

In one configuration, the first electrode and the second electrode of the sensor substrate plate are adapted to monitor biometric parameters comprising an ECG, a pulse oximetry, a temperature, a glucose level, a respiration rate, a blood pressure, an activity level, a location, and the like. In one configuration, the upper surface of the main body is concave to optimally contact the skin of the patient.

In one configuration, the electric connector of the sensor substrate plate may be mechanically adapted to connect to a power source. In one configuration, the electric connector may be mechanically and electrically adapted to connect biometric monitors comprising those for Bluetooth transmission, displaying, recording, diagnosis and/or reporting.

In one configuration, the first end portion and the second end portion have shapes of circular plates, and the first end portion, the main body, and the second end portion may form an "S" shape of the sensor substrate plate. Further, in one configuration, the sensor substrate plate may be removably held to the skin of the patient by a vest or a harness.

It is another aspect to provide a device for monitoring vital signals of a patient. In this embodiment, the device comprises a sensor substrate plate as discussed above, and a means to removably position the sensor substrate plate on the skin of a patient in order to measure a vital signal of the patient. Further, the device may comprise a first electrode mechanically and electrically connected to the first end portion of the sensor substrate plate, a second electrode mechanically and electrically connected to the second end portion of the sensor substrate plate, and a plurality of sensors or electrodes mechanically and electrically connected to the slots on the upper surface of the main body of the senor substrate plate. The device may also include an electric connector mechanically and electrically connected to the first through hole of the sensor substrate plate, and at least one monitor mechanically and electrically connected to the electric connector. In one configuration, the device may be used to monitor biometric parameters comprising an ECG, a pulse oximetry, a temperature, a glucose level, a $SpO_2$ level, a respiration rate, a blood pressure, an activity level, a location, and the like.

In one configuration, the means for removably positioning the sensor substrate plate on the skin of a patient is a vest and/or a harness. In one configuration, the plurality of sensors or electrodes are LEDs. In one configuration, the device further comprises a power source, such as a battery. In one configuration, the device is capable of monitoring biometric parameters comprising an ECG, a pulse oximetry, a temperature, a glucose level, a respiration rate, a blood pressure, an activity level, a location, etc. Further, in one configuration, the at least one monitor comprises a monitor for Bluetooth transmission, displaying, recording, diagnosis and/or reporting.

The foregoing and other aspects and advantages of the invention will appear from the following description. In the description, reference is made to the accompanying drawings which form a part hereof, and in which there is shown by way of illustration of a particular embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 6A, FIG. 6B, FIG. 6C and FIG. 6D are graphic representations showings an exemplary wet electrode applicable to the harness as discussed above according to certain embodiments of the present invention. FIG. 6A shows an isometric view of a top of the exemplary wet electrode according to certain embodiments of the present invention. FIG. 6B shows a side view of the exemplary wet electrode according to certain embodiments of the present invention. FIG. 6C is a side, cross-sectional view of the exemplary wet electrode according to certain embodiments of the present invention. FIG. 6D is an exploded view of the assembly of the exemplary wet electrode according to certain embodiments of the present invention.

FIG. 7 is a graphic representation of a top plan view of an exemplary sensor substrate plate that may be used in accordance with the harness apparatus of FIGS. 1-3, according to one embodiment;

FIG. 8A is a graphic representation showing an exemplary sensor substrate plate inserted into a harness for holding the sensor substrate plate on a patient's chest for operation thereof;

FIG. 8B is graphic representation showing another exemplary sensor substrate plate inserted into a harness for holding the sensor substrate plate on a patient's chest for operation thereof;

FIG. 14 is a diagram showing a front view of two exemplary ECG electrodes coupled to a sensor substrate plate according to one embodiment of the present invention;

FIG. 15 is a diagram showing a side view of two exemplary ECG electrodes coupled to a sensor substrate plate according to one embodiment of the present invention;

FIG. 16 is a diagram showing a side view of two exemplary ECG electrodes coupled to a sensor substrate plate according to one embodiment of the present invention;

FIG. 19 is a diagram showing an exemplary assembly of two ECG electrodes coupled to a sensor substrate plate according to one embodiment of the present invention;

FIG. 24 is a diagram showing a top view of an exemplary conducting layer of the wet electrode according to one embodiment of the present invention;

FIG. 25 is a diagram showing a side view of an exemplary conducting layer of the wet electrode according to one embodiment of the present invention;

FIG. 26 is a diagram showing a top view of an exemplary front wall of the wet electrode according to one embodiment of the present invention;

FIG. 27 is a diagram showing a side view of an exemplary front wall of the wet electrode according to one embodiment of the present invention;

FIG. 28 is a diagram showing a side view of an exemplary front wall of the wet electrode according to one embodiment of the present invention;

FIG. 29 is a diagram showing a top view of an exemplary front wall of the wet electrode according to one embodiment of the present invention;

DETAILED DESCRIPTION OF THE PREFERRED EMBODIMENT

Figure 1A:
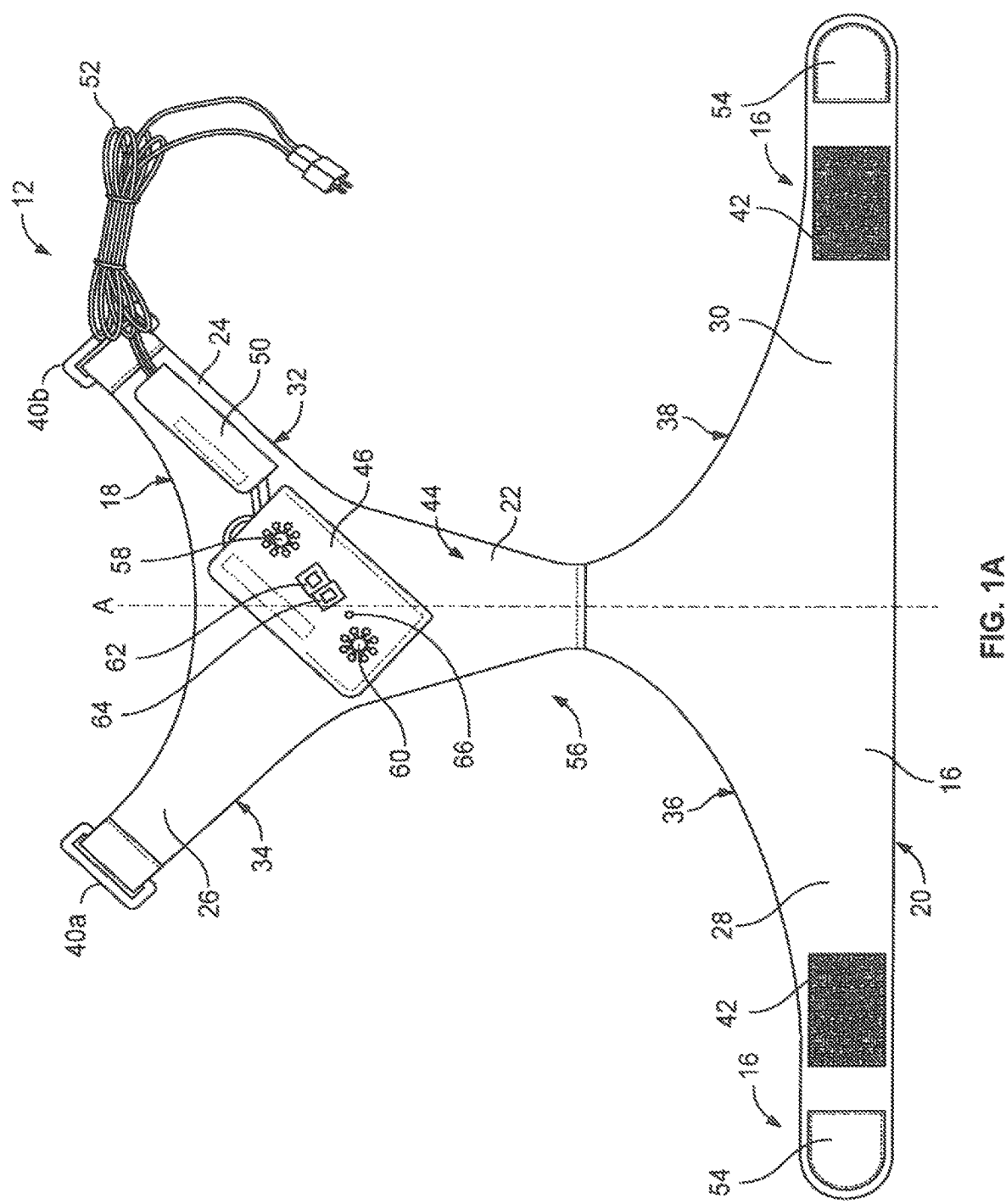
FIG. 1A is a top elevational view of an inside of a bottom portion of a harness apparatus that includes a pocket for use on an animal, according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

In some embodiments, an apparatus for the telehealth monitoring of veterinary patients is provided. In particular embodiments, the apparatus includes a veterinary sensor substrate plate and/or an ECG electrode (e.g., a wet gel ECG electrode) for non-invasively monitoring vital signals of a patients. The apparatus may be applicable to a non-human animal and, in one embodiment, the apparatus may be applicable to a patient selected from the group consisting of companion animals, primates, lab animals, pocket pets and reptiles. Throughout the application, a dog is used for demonstration purposes. However, as understood by one skilled in the art, the present invention is applicable to any companion animal, any primate, any lab animals, any pocket pet and/or any reptile.

The term "vital sign" or "vital signal," as used herein, refers to a physiological parameter of a subject (e.g., a non-human animal) and derivative parameters. In particular, the term "vital sign" or "vital signal" in this application may comprise blood volume pulse-signal, heart rate (HR) (sometimes also called a pulse rate), heart rate variability (pulse rate variability), pulsatility strength, perfusion, perfusion indicator, perfusion variability, Traube Hering Mayer waves, respiratory rate (RR), body temperature, blood pressure, a concentration of a substance in blood and/or tissue, such as a (arterial) blood oxygen saturation and/or a glucose level. Furthermore, a "vital sign" or "vital signal" in this application may also include health indications obtained from the shape of the Photoplethysmography (PPG) signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or may be even about the temperature, etc.). In one embodiment, a "vital sign" or "vital signal" refers to the measurement that indicates the state of a patient's essential body functions.

The term "subject" and/or "patient," as used herein, refers to a non-human animal. A non-human animal may comprise any companion animals, any primates, any lab animals, any pocket pets or any reptiles. In one embodiment, the non-human animal in the application is a companion animal such as a dog or a cat.

The term "measuring vital signs" or "monitoring vital signs," as used herein, may refer to measuring a variety of different vital signs (e.g., heart rate, blood pressure, and pulse oximetry). Such measurements of vital signs may help determine the physiological state of an animal and may provide necessary data in determining if the animal may require veterinary care.

The different vital signs may be further transmitted to an external controller for processing and monitoring.

The term "$SpO_2$," as used herein, refers to a peripheral capillary oxygen saturation, e.g., an estimate of the amount of oxygen in the blood.

In one aspect, a sensor substrate plate adapted to connect electrodes and/or sensors for measuring and monitoring vital signs of a subject is provided. In one embodiment, the sensor substrate plate may also be adapted to connect other necessary components including a controller or a processing system. Although specific electrodes are used as examples in the application, Applicants envision that any type or shape of electrodes may be used. For example, any ECG electrode (e.g., any wet gel ECG electrode) may be used in combination with the sensor substrate plates.

In general, vital signals may be measured as either electric signals or optical signals. For example, an electrode system with at least two electrodes may be used to generate electrical signals related to a certain skin location of a subject to generate an electrocardiogram (ECG) waveform. Alternatively, an optical system featuring a light source and a photo-detector may be used to generate an optical waveform related to the vital signs of a subject after irradiating a certain location of the skin of the subject. For example, a light-emitting diode (LED) may be used as a light source along with an optical detector to generate an optical waveform related to a vital sign of a subject. Consequently, a controller system may receive and/or process the ECG and/or the optical waveform to generate a vital sign parameter, e.g., a heart rate, a pulse oximetry, and/or a systolic and/or a diastolic blood pressure.

In one embodiment, a controller may use both electric signals and/or optical signals to produce vital sign parameters. For example, at least two electrodes may be used in the present sensor substrate plate to measure at least an electrical signal of a subject. The controller may also include an algorithm that may process the electrical signals to generate an electric waveform.

Additionally, a light-emitting diode (LED) may be used as a light source along with an optical and/or a photo-detector to measure optical signals related to a vital sign of the subject. The controller may also include an algorithm that may process the optical signals to generate an optical waveform.

The controller may then use the same or another algorithm to process the electrical waveform with the optical waveform to calculate a vital sign parameter, such as a blood pressure value. For example, the controller may determine blood pressure by processing: 1) a first time-dependent feature of the optical waveform; 2) a second time-dependent feature of the electrical waveform; and 3) a calibration parameter determined by another means (e.g., a conventional blood pressure cuff or tonometer).

In one embodiment, the sensor substrate plate or related device may be applicable to any subject during its daily life. The sensor substrate plate or related device is easily worn by an animal patient during periods of exercise and/or day-to-day activities, and may determine a non-invasive vital signal, such as blood-pressure measurement, in a matter of seconds. The resulting information has many uses for patients, medical professional, insurance companies, pharmaceutical agencies conducting clinical trials, and organizations for home-health monitoring.

In one embodiment, the sensor substrate plate and/or related device may be used in an ICU or an emergency room of a hospital to quickly assess and/or determine the condition of an animal. The sensor substrate plate or related device may also be used in any general veterinary practice and/or study of any animal and should not be limited to any specific scenario or animal.

In another embodiment, the sensor substrate plate or related device may be used in a hospital, a medical center or any other on-site clinic uses where it may be used as a substitution for the currently used devices for vital signal measurements.

FIGS. 1-4 illustrate a harness 10 with a bottom portion 12 and a top portion 14, according to one embodiment. In this particular embodiment, the bottom portion 12 and the top portion 14 are releasably attached to one another by one or more mating connectors 16. In alternative embodiments, the harness 10 may be provided as a single unitary structure. With reference to FIG. 1A, the bottom portion 12 may include a front edge 18 and a back edge 20. In this particular embodiment, the front edge 18 may be concave and the back edge 20 may be relatively planar. However, the front edge 18 and/or the back edge 20 may be relatively shaped to the specific animal the bottom portion 12 may be applied thereto. Further, the bottom portion 12 may include a central portion 22 and one or more arms or side portions 24, 26, 28, 30 extending outwardly therefrom.

In this particular embodiment, the side portions 24, 26 may be generally defined on one side thereof by the front edge 18, and by a first edge 32 and a second edge 34, respectively. Similarly, the side portions 28, 30 may be defined on one side thereof by the back edge 20, and by a third edge 36 and a fourth edge 38, respectively. In this particular embodiment, the edges 32, 34 may be relatively concave. Further, the side portions 24, 26 may have a set of hoops 40a, 40b and the side portions 28, 30 may have one or more of a loop material 42 which may be used to connect the bottom portion 12 to the top portion 14, the process of which will be discussed in further detail herein.

With further reference to FIG. 1A, an inside surface 44 of the bottom portion 12 may include a pocket 46. In this particular embodiment, the pocket 46 may be located above the central portion 22 and may be positioned between the side portions 24, 26. Further, the pocket 46 may be positioned approximately at a 45 degree angle from an axis A. In alternative embodiments, the pocket 46 may be located anywhere within or on the inside surface 44 of the bottom portion 12. In particular, the pocket 46 may be strategically located anywhere on the inside surface 44 of the bottom portion 12 to provide optimal positioning for a sensor or electrode 48 (see FIG. 7) placed therein. For example, in this particular embodiment, the sensor 48 may be used to measure and/or record an electrocardiogram of an animal. For that reason, the pocket 46 and, as a result, the sensor 48 may be located proximate to a heart of the animal. The sensor 48, and particular embodiments thereof, are discussed in more detail herein. Although the harness 10 is described for use in combination with the sensor 48, one skilled in the art would appreciate that the harness 10 may be used with a variety of sensors and, therefore, should not be limited for use with the sensor 48. Further, although in this embodiment the harness includes a pocket for placement of a sensor therein, in alternative embodiments, the sensor 48 may be directly attached to the inside surface 44 of the bottom portion 12.

The inside surface 44 of the bottom portion 12 may also include a tube 50 located on the side portion 24 and may be axially aligned, e.g., at a 45 degree angle from the axis A, with the pocket 46. As mentioned, the sensor 48 may be inserted into the pocket 46. As follows, the sensor 48 may include a set of wires 52 extending therefrom. In particular embodiments, the set of wires 52 may extend from the sensor 48 and the pocket 46, and may travel through the tube 50. As a result, the pocket 46 and the tube 50 may protect and surround the sensor 48 and the set of wires 52, respectively. Further, in some embodiments, the pocket 46 and/or the tube 50 may be formed from a Velcro® flap system, thereby allowing the sensor 48 and the set of wires 52 to be inserted therein and removed therefrom with ease.

Further, the bottom portion 12 includes a hook material 54 and a loop material (not shown) strategically located on a back-side 56 of the bottom portion 12 on the side portions 28, 30 on ends thereof. Therefore, the hook material 54 and the loop material may be used in connecting the bottom portion 12 and the top portion 14, the process of which will be discussed in further detail herein.

Figure 1B:
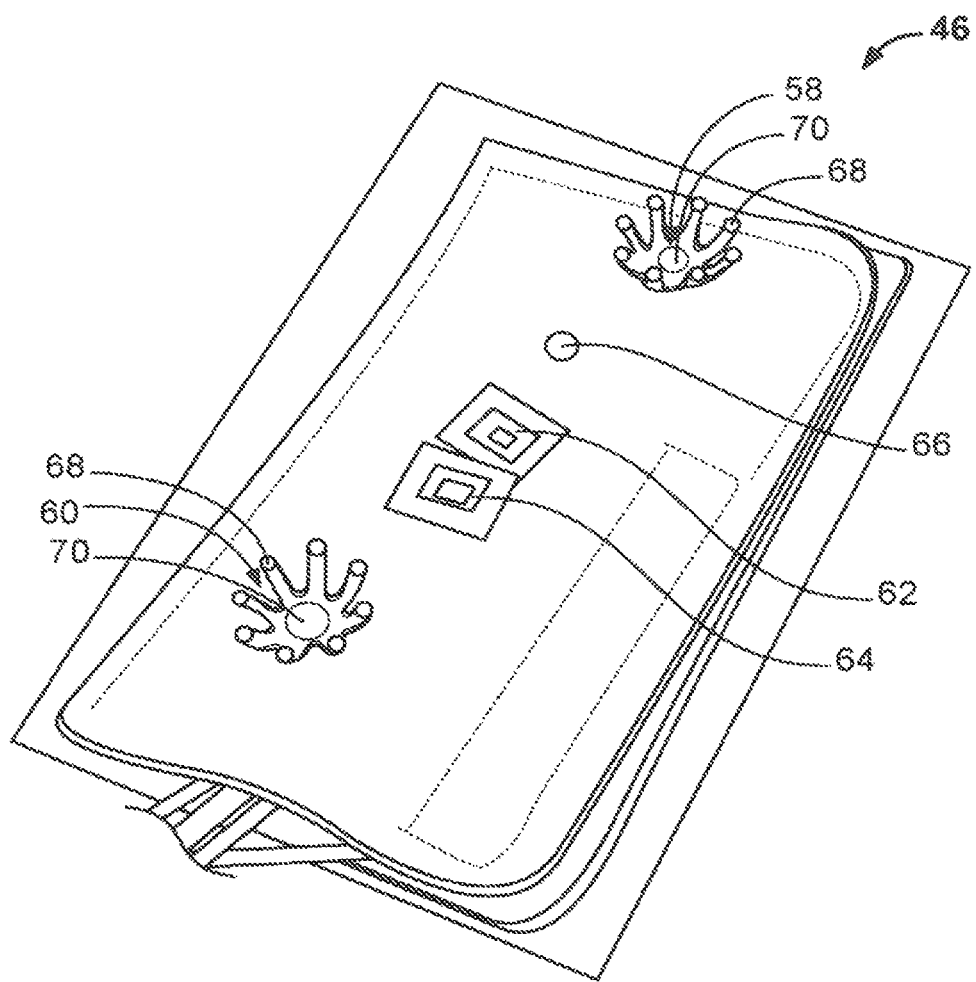
FIG. 1B is a perspective view of the pocket of the harness apparatus of FIG. 1A.

FIG. 1B illustrates an embodiment of the pocket 46 of the bottom portion 12 of the harness 10. In this embodiment, the pocket 46 includes a first transducer assembly 58 and a second transducer assembly 60. The pocket 46 may further include one or more sensor contacts, i.e., an upper sensor contact 62 and a lower sensor contact 64, and an aperture 66. In particular, the first transducer assembly 58 and the second transducer assemblies 60 may be generally "octopus-shaped" with a plurality of limbs 68 extending from a central body 70. Once positioned onto a subject, the limbs 68 of the transducer assemblies 58, 60 may penetrate through the hair of the animal the harness 10 is applied thereto. As such, the transducer assemblies 58, 60 may be used in combination with the sensor 48 to take physiological measurements with or without having to shave a particular area of the animal the sensor 48 and the pocket 46 is applied thereon. A preferred embodiment of the transducer assemblies 58, 60 is described in detail in U.S. Pat. No. 9,314,183, the entirety of which is incorporated by reference, herein.

In some embodiments, the sensor 48 may be used in combination with an ECG pad electrode or an alligator clip electrode. Further, the sensor contacts 62, 64 may be for use with a plurality of LEDs. In a particular embodiment, the sensor contacts 62, 64 are $SpO_2$ reflective sensors. Therefore, in this embodiment, the $SpO_2$ reflective sensors may be used to provide capillary bed measurements in order to determine the $SpO_2$ or oxygen saturation levels of a subject. The aperture 66 may also be used in conjunction with the sensor 48 to provide for a temperature reading, a glucose reading, and/or any other desired physiological measurement of a subject. In alternative embodiments, the pocket 46 is adapted for a unique sensor placed therein. The sensor 48 may be used to measure a plurality of physiological measurements of an animal including an electrocardiogram, an electrocardiograph, an oxygen saturation measurement, a heart rate, a temperature, a glucose level, a respiration rate, a blood pressure, a pulse oximetry, or any other vital sign. In further embodiments, the sensor 48 may also be an accelerometer. And so, the pocket 46 may be further adapted, in some embodiments, to fit a particular sensor positioned therein.

Figure 1C:
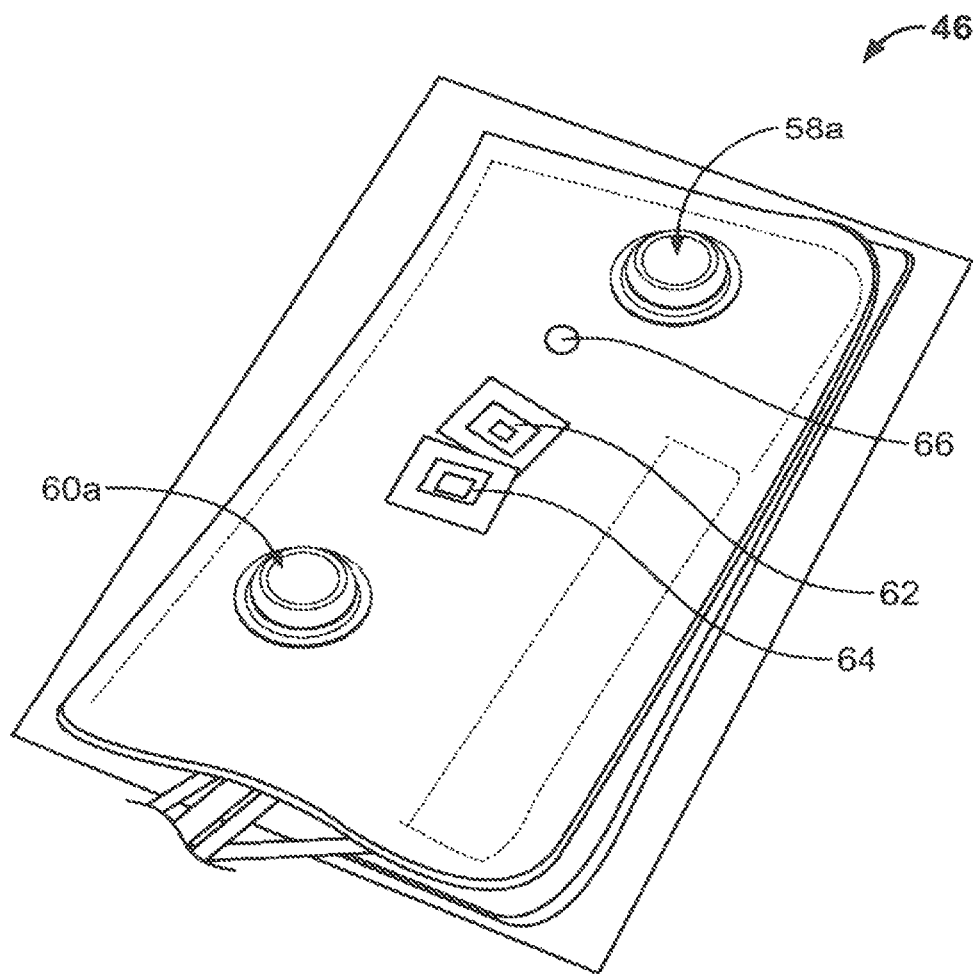
FIG. 1C is a perspective view of the pocket of the harness apparatus of FIG. 1A including wet electrodes, according to one embodiment of the invention.

FIG. 1C illustrates another embodiment of the pocket 46 of the bottom portion 12 of the harness 10. In this particular embodiment, the pocket 46 may include a first transducer or first wet electrode 58a and a second transducer or second wet electrode 60a. The pocket also includes the upper sensor contact 62 and/or the lower sensor contact 64, and/or the aperture 66. In particular embodiments, the first wet electrode 58a and/or the second wet electrode 60a may be used in combination with the sensor 48 to take physiological measurements with or without having to shave a particular area of the animal the sensor 48 and the pocket 46 is applied thereon.

Figure 2:
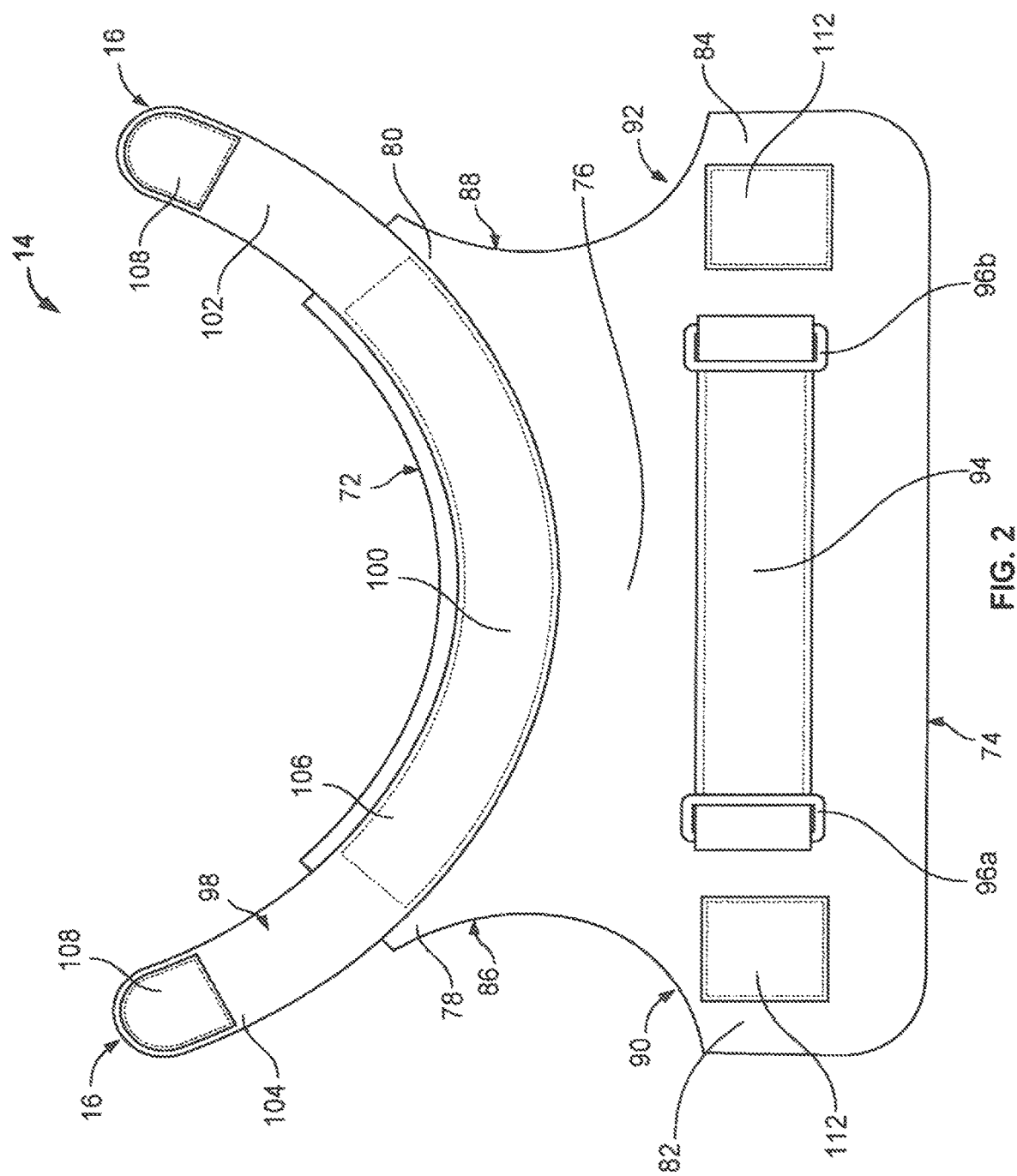
FIG. 2 is a top elevational view of a top portion for use in conjunction with the bottom portion of the harness of FIG. 1A to form the harness of the harness apparatus for use on an animal, according to one embodiment of the invention.

Looking to FIG. 2, the top portion 14 includes a front edge 72 and a back edge 74. In this particular embodiment, the front edge 72 may be concave and the back edge 74 may be relatively planar. The top portion 14 further includes a central portion 76 and a plurality of side portions 78, 80, 82, 84 extending therefrom.

The side portions 78, 80 may be defined on one side thereof by the front edge 72 and relatively concave edges 86, 88, respectively. Similarly, the side portions 82, 84 may be defined on one side thereof by the back edge 74 and relatively concave edges 90, 92, respectively. However, similar to the bottom portion 12, the front edge 72 and the back edge 74 may be relatively shaped for a specific animal the top portion 14 may be applied thereto. Further, the top portion 14 may include a belt 94 with a set of hoops 96a, 96b located on the side portions 82, 84. The hoops 96a, 96b may be use to connect the bottom portion 12 to the top portion 14.

The top portion 14 further includes an extension material 98 that may be relatively semi-circle, and may comprise a body portion 100, and one or more of extensions 102, 104. In this particular embodiment, the body portion 100 may be positioned on the top portion 14 and the extensions 102, 104 may extend from the side portions 78, 80, respectively. The body portion 100 may comprise a surface comprising a hook material 106. In this embodiment, the hook material 106 may cover the entirety of the body portion 100. In further embodiments, the hook material 106 may only partially cover the body portion 100. In the present embodiment, the extensions 102, 104 comprise a loop material 108 located on the extensions 102, 104. Further, the loop material 108 may be positioned on the end of the extensions 102, 104. The top portion 14 may also include an aperture 114 (see FIG. 3A) that is relatively rectangular. Further, the top portion includes a plurality of hook material 112 positioned on the side portions 82, 84.

Figure 3A:
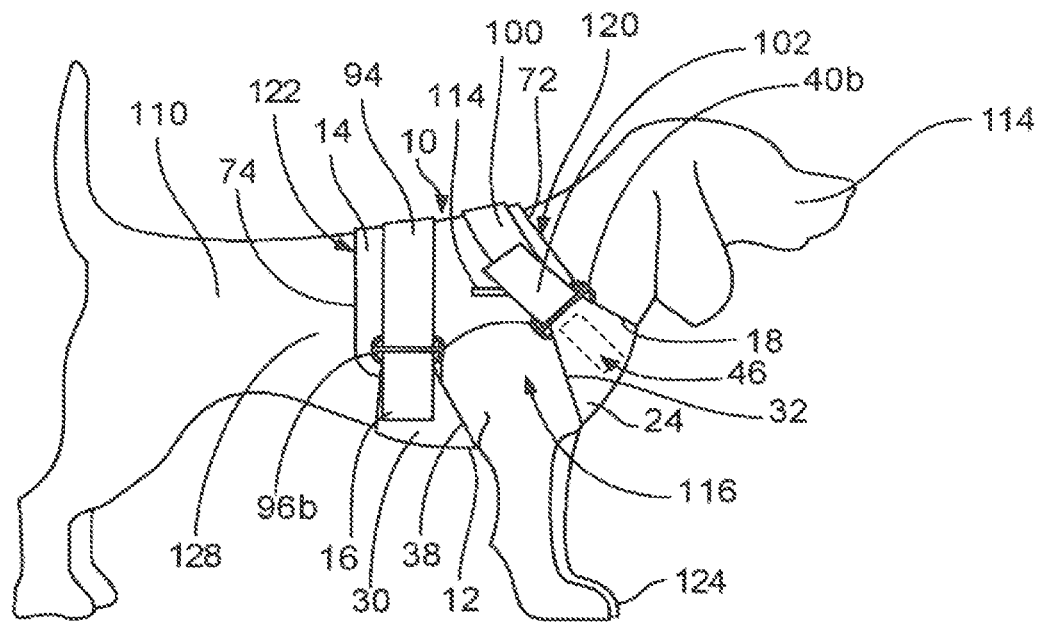
FIG. 3A illustrates a right side elevational view of a dog wearing an embodiment of the harness apparatus including a sensor substrate plate.
Figure 3B:
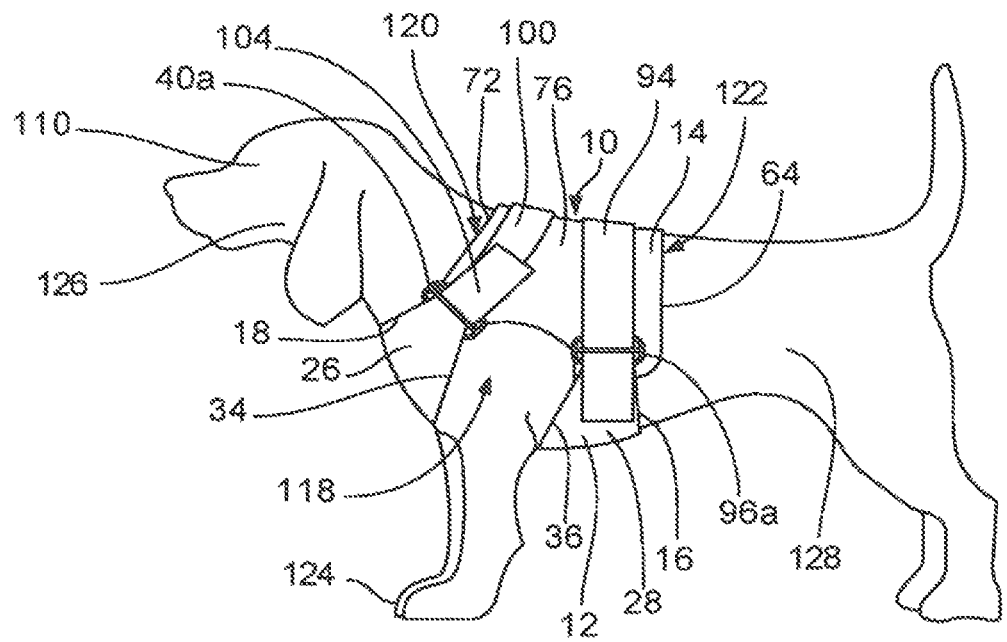
FIG. 3B is a left side elevational view of the dog of FIG. 3A.

FIGS. 3A-B illustrate the harness 10 on a dog 110. However, it should be understood, that the harness 10 may be used on a range of animals further including cats, primates, mice, rats, hippopotamuses, horses, dolphins, and such. In this particular embodiment, the harness 10 comprises the aforementioned bottom portion 12 and the top portion 14. In this embodiment, the bottom portion 12 and the top portion 14 have a plurality of matting connectors 16 in the form of hook and loop material, e.g., Velcro® material. However, it should be understood that in other embodiments, any aforesaid reference to a hook material may be substituted with a loop material, and vice versa. Further, in yet further embodiments, the matting connectors 16 may be a belt, a set of straps comprising one or more buckles, an adhesive, or any material and/or device capable of connecting the bottom portion 12 to the top portion 14. As previously mentioned, the harness 10 may also be provided as a unitary structure and, therefore, may not require matting connectors.

With reference to FIGS. 3A-B, the bottom portion 12 and the top portion 14 are connected as follows. The hook material 112 may be connected to the loop material 42. Further, the side portions 28, 30 may be inserted within the hoops 96a, 96b and folded to connect the hook material 54 with the loop material (not shown) on the back-side 56 of the bottom portion 12. Additionally, the extensions 102, 104 may be inserted within the hoops 40a, 40b and folded to connect the hook material 106 with the loop material 108. Therefore, after doing so, a user may apply the harness 10 to the dog 110. Once connected, the bottom portion 12 and the top portion 14 may form one or more apertures 116, 118, 120, 122. In this particular embodiment, the apertures 116, 118 may provide holes for the insertion of a pair of front legs 124 of the dog 110. Further, the aperture 120 may provide a hole from which a head 126 of the dog 110 may extend therefrom and the aperture 122 may provide a hole from which a hind body 128 of the dog 110 may extend therefrom.

In this particular embodiment, the bottom portion 12 has a relatively concave shape that closely mimics a shape of a chest of the dog 110. As a result, the pocket 46, which includes the sensor 48 may closely adhere to the body of the dog 110 and may give the sensor 48 an improved connection with the body of the dog 110. Further, in the preferred embodiment, the sensor 48 may also be relatively concave in shape to similarly mimic the shape of the chest of the dog 110. The combination of the unique concave fit of the bottom portion 12 and the pocket 46, with the transducer assemblies 58, 60 allows for an accurate measurement of vital components without the animal being required to be shaven or without the use of adhesives. Further, the aforementioned properties allows for increased mobility for the dog 110.

Figure 4:
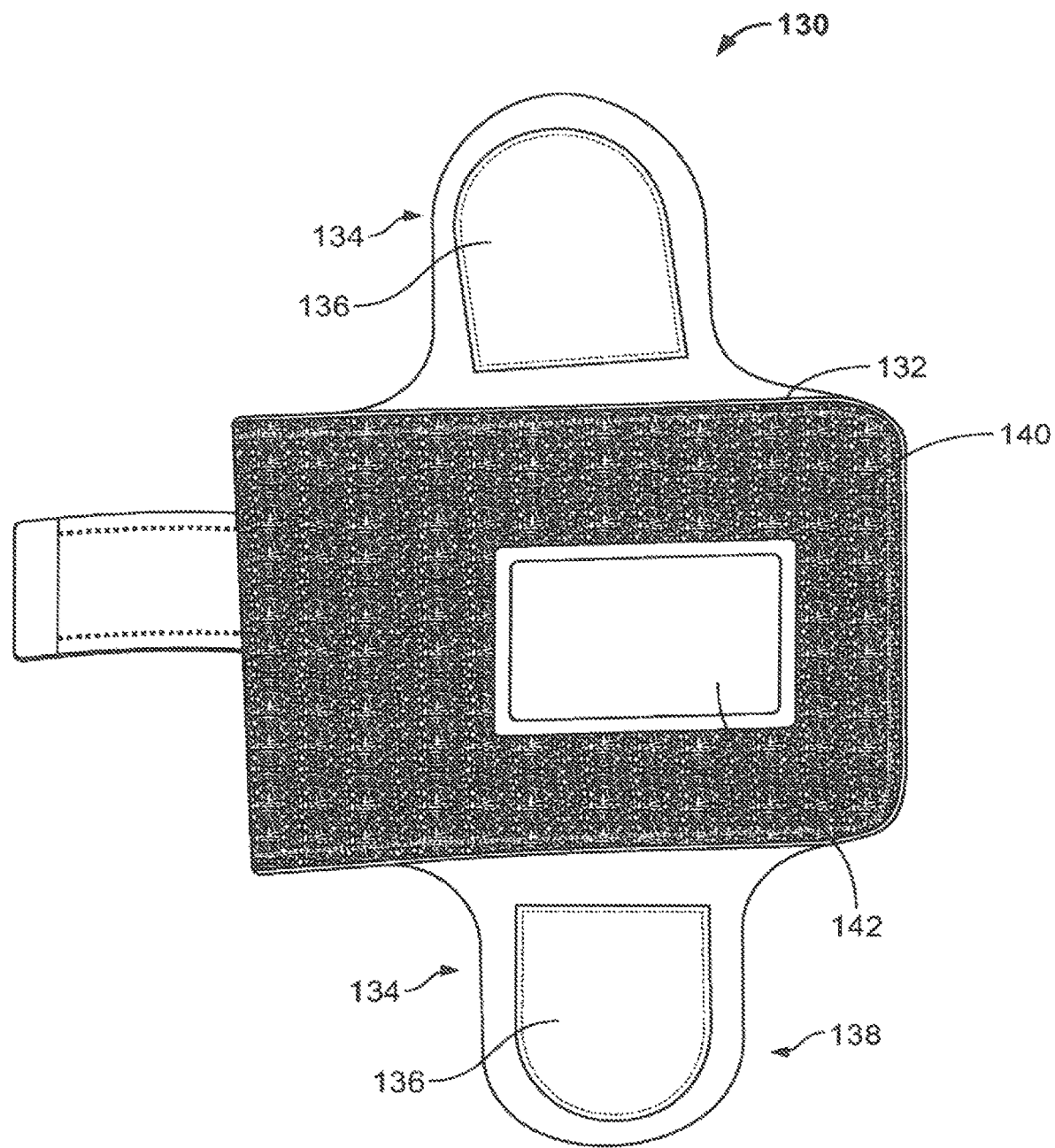
FIG. 4 is a top elevational view of a case for use with the harness of FIGS. 1A-3B, according to one embodiment of the invention.

FIG. 4 illustrates a top elevational view of a case 130 that may be releasably attached to the harness 10. In a particular embodiment, the case 130 may be releasably attached to an outside portion of the top portion 14 of the harness 10. The case 130 includes a body portion 132 that is relatively square or rectangular in shape and a plurality of flanges 134 extending from the body portion 132. In this particular embodiment, the flanges 134 include a Velcro® material and/or an adhesive material 136 on a back side 138 of the flanges 134. Further, in this embodiment, an outside of the top portion 14 may be substantially made of a material that may adhere to the adhesive material 136. For example, the adhesive material 136 may be a hook material for a Velcro® connection and the outside of the top portion 14 may be substantially made from a loop material for a Velcro® connection. Therefore, the case 130 may be releasably attached to the top portion 14 with ease. In alternative embodiments, the case 130 may be releasably attached to the top portion 14 using straps or other suitable mechanisms.

The case 130 may further include a pocket 140 and a transparent section 142. Therefore, a monitoring device 144 (see FIG. 5) may be inserted within the pocket 140 and observed through the transparent section 142. In a particular embodiment, the monitoring device 144 may be a battery operated unit, such as a Vetcorder Home™ provided by Sentier™. In this particular embodiment, the sensor 48 may be connected to the monitoring device 144 by the set of wires 52. Further, the set of wires 52 may travel from the pocket 46, through the tube 50 and the aperture 114, and may connect to the monitoring device 144 in the pocket 140. To that end, the set of wires 52 may be continuously covered and protected by the harness 10.

Figure 5:
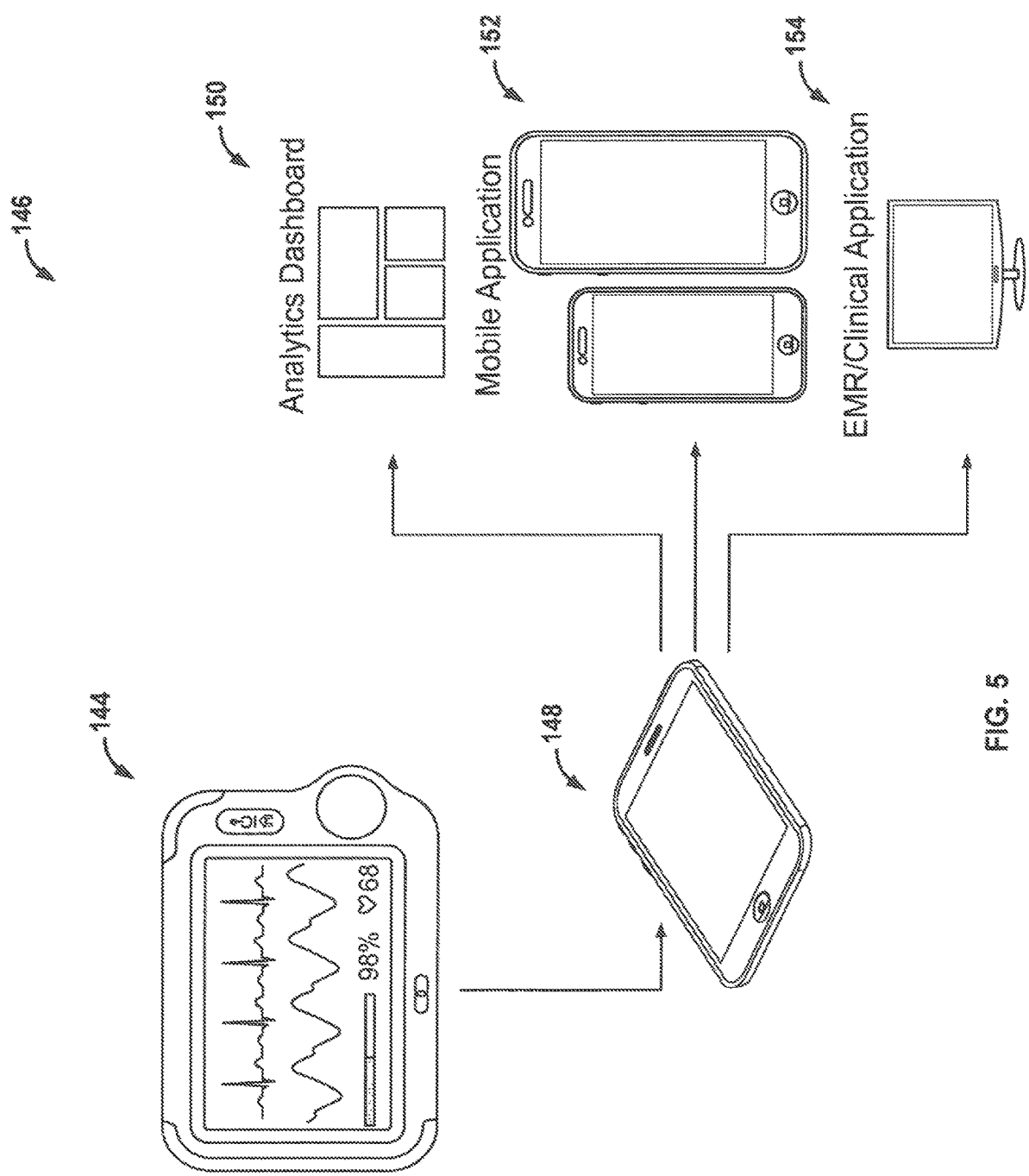
FIG. 5 is a graphic representation of a monitoring system including the harness apparatus of FIGS. 1-3 and a monitoring device.

As shown in FIG. 5, the harness 10 may be used in conjunction with a monitoring system 146 that includes the monitoring device 144. Further, the monitoring device 144 may be also connected to a computer 148, e.g., a personal computer, a cellular device, or the like, and a cloud database (not shown). In some embodiments, the computer 148 may include and/or may be further connected to an analytics dashboard 150, a mobile application 152, and/or an EMR or clinical application 154. In particular, the monitoring device 144 may process and store data acquired from the sensor 48 and then may transit the acquired data to the computer 148. The monitoring device 144 may transit the acquired data by a wireless connection or may transmit the data using a wired connection using a wire (not shown). As such, the monitoring system 146 may allow for monitoring of a subject at any location and may allow for big data applications.

Although the monitoring system 146 is discussed in connection with the harness 10 and the sensor 48, an invasive and/or internal sensor (not shown) may be used in the monitoring system 146. In particular embodiments, a subject may include an internal sensor positioned in a body thereof. In this embodiment, the internal sensor may also be capable of transmitting a plurality of vitals or vital signs to the monitoring system 144. For example, the internal sensor may be a $SpO_2$ reflective sensor used to provide capillary bed measurements in order to determine the $SpO_2$ or oxygen saturation levels of a subject. In further embodiments, the internal sensor may provide a temperature reading, a glucose reading, an electrocardiogram, an electrocardiograph, an oxygen saturation measurement, a heart rate, a temperature, a glucose level, a respiration rate, a blood pressure, a pulse oximetry, and/or any other vital sign. In further embodiments, the internal sensor may also be an accelerometer.

The harness 10, the sensor 48, and the monitoring device 144 may be used in a combination of instances. For instance, the harness 10, the sensor 48, and/or the monitoring device 144 may be purchased by an animal owner that wishes to monitor a status or a health of their animal. In this case, the harness 10, the sensor 48, and/or the monitoring device 144 may be used on a spot check basis. However, more particularly, the harness 10, the sensor 48, and/or the monitoring device 144 may be used by animal owners with animals that have prior health concerns. As such, the harness 10, the sensor 48, and/or the monitoring device 144 may be used to monitor specific physiological characteristics of an animal to help determine the health of said animal. For example, the harness 10, the sensor 48, and/or the monitoring device 144 may be provided to an animal undergoing chemotherapy for consistent monitoring of vital signs of the animal. In an alternative embodiment, the harness 10, the sensor 48, and/or the monitoring device 144 may be used in animal testing. In yet another embodiment, the harness 10, the sensor 48, and/or the monitoring device 144 may be used in an ICU or an emergency room of a hospital to quickly assess and determine the condition of an animal. In short, the harness 10, the sensor 48, and/or the monitoring device 144 may be used in any general veterinary practice and/or study of any animal and should not be limited to any specific scenario or animal.

The harness 10 may be made from a variety of materials. In particular, the harness 10 may be designed to be lightweight, comfortable, and adjustable. In a particular embodiment, the harness 10 may be made out of a material under the product name Breathe-O-Prene®. However, it should be understood that the harness 10 may be made out of any other suitable material.

It should be appreciated by those skilled in the art, that although the bottom portion 12 and the top portion 14 have been described in this embodiment, the bottom portion 12 and the top portion 14 may have a plurality of shapes and sizes to fit an animal in which the harness 10 may be applied thereto. For example, the harness 10 may be used on a range of animals including in a wild animal or a domestic animal such as a dog, a cat, a primate, a mouse, a rat, a hippopotamus, a horse, a pocket pet and the like. As such, the size and shape of the harness 10 should not be limited to the aforementioned embodiment, but instead should be unique to the particular animal applied thereto. Additionally, in some embodiments, the harness 10 may be provided as a unitary structure. In this particular embodiment, the bottom portion 12 and the top portion 14 may be provided as one unit.

In another aspect, the present application discloses an electrode, such as a wet electrode. In one embodiment, the wet electrode or any sensor including such a wet electrode does not require hair removal of the subject's skin before its application. In one embodiment, the wet electrode is a wet electrocardiography (ECG or EKG) electrode such as a wet gel ECG electrode.

In one embodiment, the wet electrode may be used in combination with any other electrode or sensors or devices.

In one specific embodiment, the wet electrode may be directed and removably attached to the inside surface of a harness such as the one disclosed herein. For example, one or more wet electrodes 58a, 60a may be coupled in the inner surface of the harness as shown in FIGS. 1-3.

In another embodiment, the wet electrodes 58a, 60a may be directly coupled to a sensor substrate plate before it is used in a harness such as the one disclosed herein.

FIGS. 6A-6D provide systematic diagrams of an exemplary wet electrode 600 that may be used for the wet electrodes 58a, 60a according to certain embodiments of the application.

In one embodiment, the wet electrode 600 may be capable of directly attaching to the skin of a patient to measure vital signals of the patient. A sensor or device using the wet electrode of the present invention allows one to directly apply the sensor or device on the skin of a subject without the need of hair removal of the contact skin.

Figure 6D:
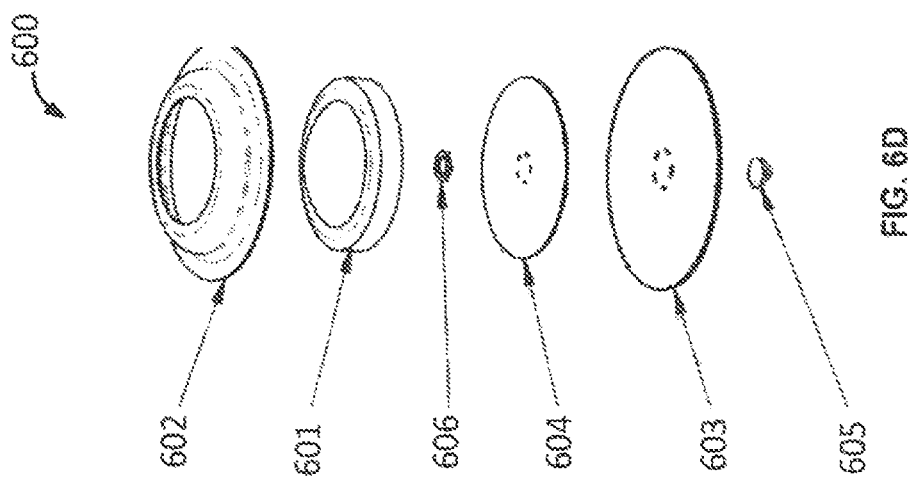

Referring to FIGS. 6A, 6B, 6C, and 6D, in one embodiment, the wet electrode 600 comprises a housing comprising a front wall 602 having an opening in the central part thereof and a back wall 603 having a through hole therein. Further, the wet electrode 600 comprises a main body 601 held within the housing, where at least part of the main body 601 may be exposed through the opening of the front wall 602 of the housing. Additionally, the wet electrode 600 may include a conducting layer 604 between the main body 601 and the back wall 603 of the housing, an electrical connector assembly including a conducting pin 605 fastened to a fastener 606 and the assembly holds the metal substrate or a mash and the back wall 603 of the housing via the through hole on the back wall 603. In particular, FIG. 6D shows assembly of the exemplary wet electrode 600 according to certain embodiments of the present invention.

Although the wet electrode 600 in FIGS. 6A, 6B, 6C and 6D is described as being circular, any other shape as appreciated by one skilled in the art could be used as the wet electrode.

In one embodiment, the front wall 602 may be made of a non-conductive polymer material, which provides support of the housing to the main body 601. In one embodiment, the front wall 602 may be made of a thermoformed polymer.

In one embodiment, the back wall 603 may be made of a non-conductive polymer material. In one specific embodiment, the back wall 603 may comprise a means of attachment such as an adhesive layer or a Velcro on its opposing side to the front wall 602 so that the web electrode can removably attach to another surface.

As shown in FIGS. 6C and 6D, the edge of the front wall 602 may be coupled to the edge of the back wall 603 to form the housing. In one embodiment, the edge of the front wall 602 may be coupled to the edge of the back wall 603 through any suitable appreciated by one skilled in the art. For example, the edge of the front wall 602 may be glued, heat staked, heat welded or solvent welded to the edge of the back wall 603 to form the housing.

In one embodiment, the main body 601 may be made of a stretchable material such as a polymer material capable of absorbing liquid materials. In one embodiment, the main body 601 may be made of a sponge or a similar material.

In one embodiment, the main body 601 of the wet electrode 600 may absorb at least one conductive liquid material. When the main body 601 of the wet electrode 600 may be in close contact with the skin of a subject, the conductive liquid material within the main body 601 of the wet electrode 600 may provide sufficient conductivity between the contact surface and the metal substrate or mash. Hair removal or shaving is thus not necessary for the subject.

As shown in FIG. 6C, at least part of the main body 601 may be exposed so that during the application of the wet electrode 600, at least part of the main body 601 may be attached to the skin of a subject. In one embodiment, the subject does not need to remove hair on the contact skin. The wet electrode 600 with at least part of the main body 601 with a conductive liquid material may be directly applied to the subject without the need of shaving and hair removal.

In one embodiment, the conducting layer 604 may be a stainless steel mesh. As shown in FIGS. 6C and 6D, the conducting layer 604 may be coupled to the electrical connector assembly where the conducting pin 605 may be fastened to the fastener 606, providing the necessary additional conductivity of the wet electrode.

Electrical contact may be established between the conducting layer 604 and the conducting pin 605 by fastening the conducting pin 605 to the fastener 606. The conducting pin 605 may be used to connect to a monitoring unit, as described with reference herein. In some implementations, the fastener 606 may also be electrically conducting. The conducting pin 605 and the fastener 606 may form a snap assembly.

The electrical connector assembly through the conducting pin 605 and the fastener 606 provides connection to wires or cables to connect to controllers, processors or monitors (not shown). As such, the wet electrode 600 may detect the tiny electrical changes on the skin (without the need of hair removal) that arise from the heart muscle's electrophysiologic pattern of depolarizing and repolarizing during each heartbeat.

In one embodiment, the wet electrode 600 of the present application may be coupled to the harness of the present application.

In one embodiment, the wet electrode 600 of the present application may be coupled to a sensor substrate plate such as those disclosed herein.

In another aspect, the application discloses a sensor substrate plate. In one embodiment, the sensor substrate plate may hold one single electrode. FIGS. 6A-6D disclose a sensor substrate plate that can hold one single electrode (e.g., one single wet electrode).

In another embodiment, the sensor substrate plate can hold two or more electrodes (e.g., two or more wet electrodes).

Referring to FIG. 7, a top view of a sensor substrate plate 700 that may be used as the sensor 48 and/or as the wet electrode 600 is shown. The sensor substrate plate 700 may be made of any polymer, rubber or non-conductive material. In one embodiment, the sensor substrate plate 700 may be made of a polymer material. For example, one exemplary sensor substrate plate 700 may be made of a polyoxymethylene (POM) (also known as acetal, polyacetal and polyformaldehyde). A typical example of the commercial product is DuPont's DELRIN.

Figure 12A:

In another embodiment, the sensor substrate plate 700 may be made of a rubber-like material such as TangoGray™, TangoBlack™, TangoPlus™ or TangoBlackPlus™. FIG. 12A shows an exemplary sensor substrate plate may be made of TangoGrey™.

Additionally, the sensor substrate plate 700 may also be made of a high-speed liquid photopolymer that can produce flexible, high-impact strength, accurate parts. The example of such photopolymer is Somos® 8120. FIGS. 10B, 10C, 10D and 10E show exemplary sensor substrate plates made of Somos® 8120.

The sensor substrate plate 700 may have different colors depending on the materials of which it is made. Applicants envision that a sensor substrate plate 700 may have any color by adding the specific color agent into to the material or by color-coating the surface of the material.

Referring to FIG. 7, the sensor substrate plate 700 comprises an elongated main body 701. The main body 701 and the sensor substrate plate 700 may be substantially flat and/or may be made of a polymer or rubber-like, semi-rigid material. The main body 701 may comprise an upper surface 702 and an under surface (not shown). In one embodiment, the upper surface 702 of the main body 701 may be configured to removably contact the skin surface of a patient. For example, the upper surface 702 may be slightly concave to consist with the contour of the skin surface of a patient so that the main body 701 and the sensor substrate plate 700 may closely contact the skin surface of the patient.

In one embodiment, the main body further comprises a plurality of slots 703 on the upper surface 702 of the main body 701. The plurality of slots 703 may be configured to hold sensors or electrodes (such as the wet electrodes 600) for monitoring biometric parameters of the patient. In one embodiment, the plurality of slots 703 may comprise two slots.

In one embodiment, the main body 701 may further comprise a first through hole 704 configured to hold an electrical connector (not shown).

In one embodiment, an electric connector may be place on any other location on the sensor substrate plate 700.

In another embodiment, the first through hole 704 may be configured to hold a probe or a sensor for temperature and/or glucose measurement (not shown). In yet another embodiment, a probe and/or a sensor for temperature and/or glucose measurement may be placed on any other location on the sensor substrate plate 700.

In one embodiment, the main body 701 may further comprise a first end 705 and a second end 706 of the main body 701.

As shown in FIG. 7, the sensor substrate plate 700 may comprise a first end portion 707 that may be integrated to the first end 705 of the main body 701. In one embodiment, the first end portion 707 may comprise a second through hole 709. Further, the second hole 709 may be configured to hold a first electrode (e.g., the wet electrode 600; not shown).

Similarly, the sensor substrate plate 700 may comprise a second end portion 708 that is coupled to the second end 706 of the main body 701. In one embodiment, the second end portion 708 comprises a third through hole 710. The third through hole 710 may be configured to hold a second electrode (e.g., the wet electrode 600; not shown).

In one embodiment, as shown in FIG. 7, the first end portion 707 and the second end portion 708 may have shapes of circular plates and wherein the first end portion 707, the main body 701 and the second end portion 708 may form an "S" shape of the whole sensor substrate plate 700. Alternative shapes of the first end portion 707 and the second end portion 708 may also be used for the present invention. Further, any shape of the first end portion 707 and/or the second end portion 708 may also be used to consist with any specific shape of an ECG electrode, e.g., a wet ECG electrode or a wet gel ECG electrode. FIGS. 13-38 disclose specific examples of wet ECG electrodes and their components with the sensor substrate plates.

Further, the sensor substrate plates of the application may also be combined with other types of electrodes.

In one embodiment, when the first end portion 707 and the second end portion 708 have shapes of circular plates, the second through hole 709 and/or the third through hole 710 may be located in the centers of the first end portion 707 and the second end portion 708, respectively.

In one embodiment, the sensor substrate plate 700 may be applicable to a non-human animal patient. In one embodiment, the patient may be selected from the group consisting of companion animals, primates, lab animals, pocket pets and reptiles. In one specific embodiment, the patient is a dog.

In one embodiment, the sensor substrate plate 700 may allow the first wet electrode 58a and/or the second wet electrode 60a to monitor biometric parameters of two different tissues of the patient. For this purpose, the size of the sensor substrate plate 700, i.e., the length of the main body 701, and the sizes of the first end portion 707 and the second end portion 708, may be varied depending on the type of animals or the size of the animals.

For example, when the patient is a dog as shown in FIG. 8A and FIG. 8B, the sensor substrate plate 700 may have a specific size so that the first wet electrode 58a (i.e., the center of the first end portion 707) would be positioned to measure vital signals of the upper chest of one side of the dog and the second wet electrode 60a (i.e., the center of the second end portion 708) may be positioned to measure vital signals of the abdomen of the opposite side of the dog. As such, the second wet electrode 60a may be positioned to measure vital signals of the left leg axis of the dog patient's heart.

In one embodiment, the first wet electrode 58a may be positioned to monitor the upper right chest of the patient and the second wet electrode 60a may be positioned to monitor the left leg axis of the patient's heart.

Figure 9:
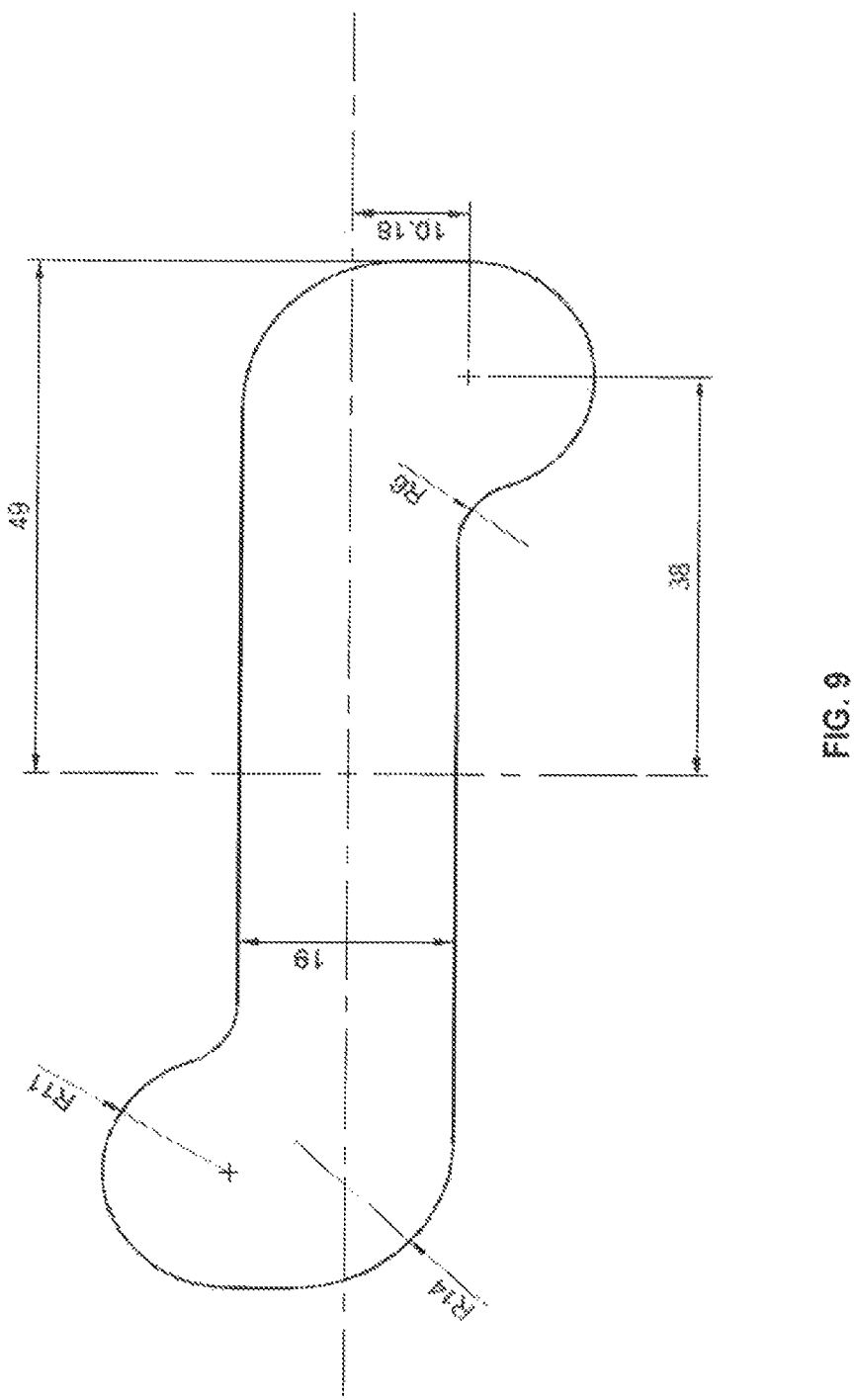
FIG. 9 is a graphic representation of a top view plan of an exemplary sensor substrate plate according to one embodiment of the present invention.
Figures 10C, 10D, 10E:
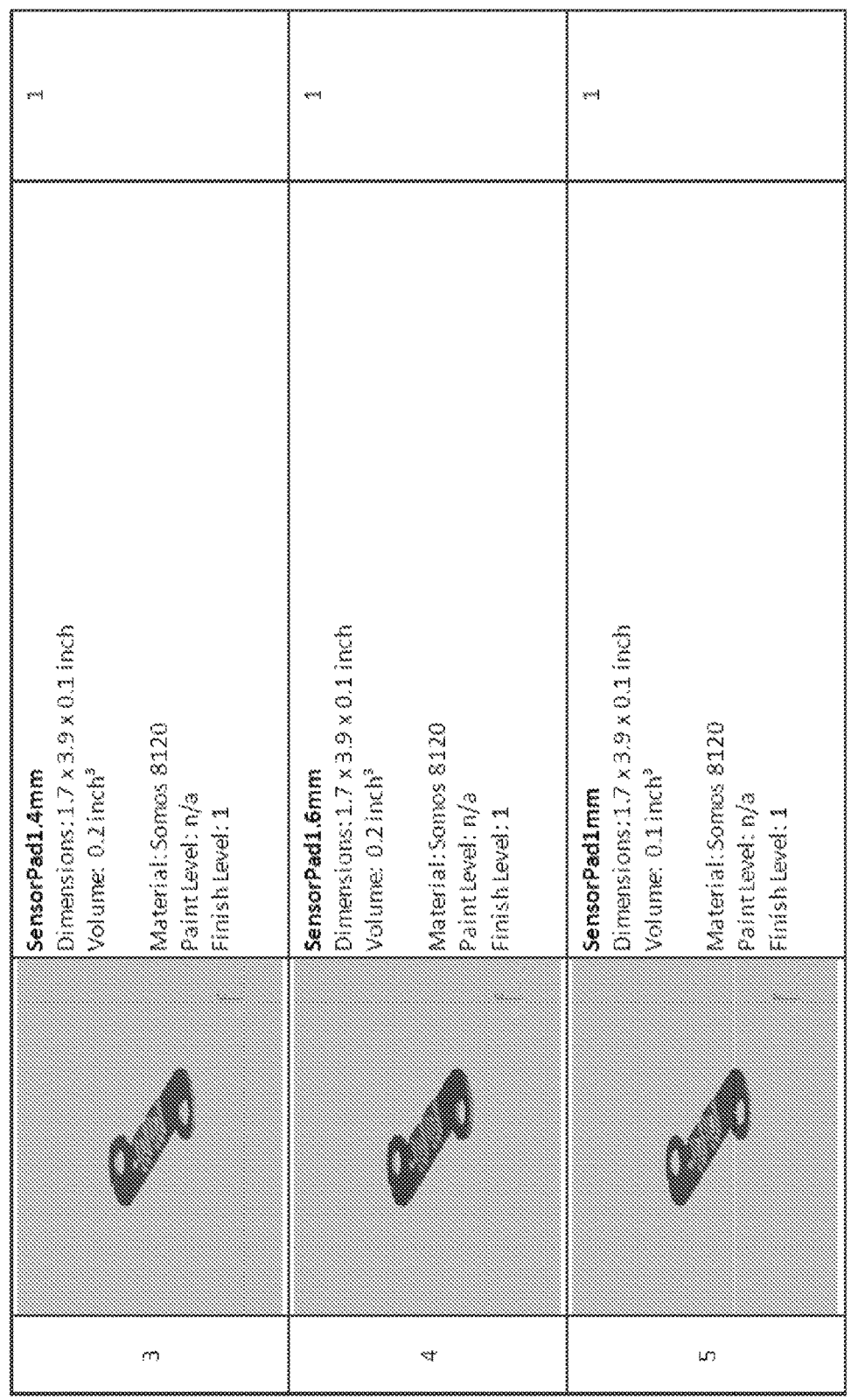
FIGS. 10, 11, and 12 A-B are Intentionally Omitted.
Figure 11:

FIG. 9 shows an exemplary sensor substrate plate with a specific dimension suitable for a dog patient.

The present invention may also cover various dimensions of sensor substrate plates that consist with the sizes of an animal patient, such as any companion animal, any primate, any lab animal, any pocket pet or any reptile.

In one embodiment, the sensor substrate plates may be made of a flexible or a semi-rigid material. For example, the upper surface 702 of the sensor substrate plate 700 may be easily bent to fit the contour of the skin surface of a subject. As such, the majority of the upper surface 702 may closely contact the skin surface of the subject.

In one embodiment, the upper surface 702 of the main body 701 may be slightly concave to optimally contact the skin of the patient.

In one embodiment, the upper surface 702 may be configured to removably contact the skin surface of the patient. For example, the upper surface 702 of the sensor substrate plate may be attached to the skin surface by using a suitable tape, a glue or adhesive or any other attachment method as appreciated by one skilled in the art.

In one embodiment, the upper surface 702 may be removably attached to the skin surface of a patient by using a vest or a harness.

Further, the sensor substrate plate 700 may also hold two sensors or electrode assemblies through the plurality of slots 703 in the main body 701. In one embodiment, two sensors or electrode assemblies may include LEDs and optical or photo-detectors (see e.g., FIG. 28). Similarly, the sensors or electrode assemblies such LEDs or optical detector may also include necessary wires or cables to connect to controllers, processors or monitors (not shown).

In one embodiment, the first wet electrode 58a and/or the second wet electrode 60a, and their assemblies may be adapted to monitor biometric parameters including ECG, pulse oximetry, temperature glucose, respiration rate, a glucose level, a $SpO_2$ level, blood pressure, activity level, location and others. In one embodiment, the first wet electrode 58a and/or the second wet electrode 60a may be wet gel ECG electrodes. FIGS. 13-38 disclose specific examples of wet gel ECG electrodes coupled with the sensor substrate plates. Such measurements on these parameters help determine the physiological state of an animal and may provide necessary data in determining if the animal may require veterinary care.

In one embodiment, the first through hole 704 may be located between the first end portion 707 and the plurality of slots 703 of the main body 701. Alternatively, the first through hole 704 may be located on any place of the upper surface 702 of the sensor substrate plate 700. The first through hole 704 may be located among the plurality of slots 703 or a place between the plurality of slots 703 and the second end portion 708.

In one embodiment, the first through hole 704 may be used to mechanically connect to a temperature or glucose sensor or probe.

In one embodiment, a temperature or glucose sensor or probe may be on any place of the upper surface 702 of the sensor substrate plate 700.

In one embodiment, the first through hole 704 may be used to couple to an electrical connector.

In one embodiment, the electrical connector may be on any place of the upper surface 702 of the sensor substrate plate 700.

In one embodiment, the electric connector may be mechanically and electrically adapted to connect a power source (not shown). Any power source appreciated by one skilled in the art may be used in the present invention. In one embodiment, the power source may be a battery.

In one embodiment, the electrical connector may be adapted to connect biometric monitors comprising those for Bluetooth transmission, displaying, recording, diagnosis or reporting. For example, the electric connector may connect the electrode assemblies, LEDs and optical detectors assemblies to biometric monitors of Bluetooth transmission, displaying, recording, diagnosis or reporting.

In one embodiment, the plurality of slots 703 on the upper surface 702 of the main body 701 may be mechanically and electrically configured to hold sensors or electrodes assemblies for monitoring biometric parameters comprising ECG, pulse oximetry, temperature glucose, respiration rate, a glucose level, an $SpO_2$ level, blood pressure, activity level, location and others.

In one embodiment, the plurality of slots 703 may hold LEDs and/or optical or photo-detectors.

In one embodiment, one of the plurality of slots 703 holds a dual LED (one visible LED and one infrared LED) and one of the plurality of slots 703 holds a photo-detector.

Figure 12B:
Figure 13:
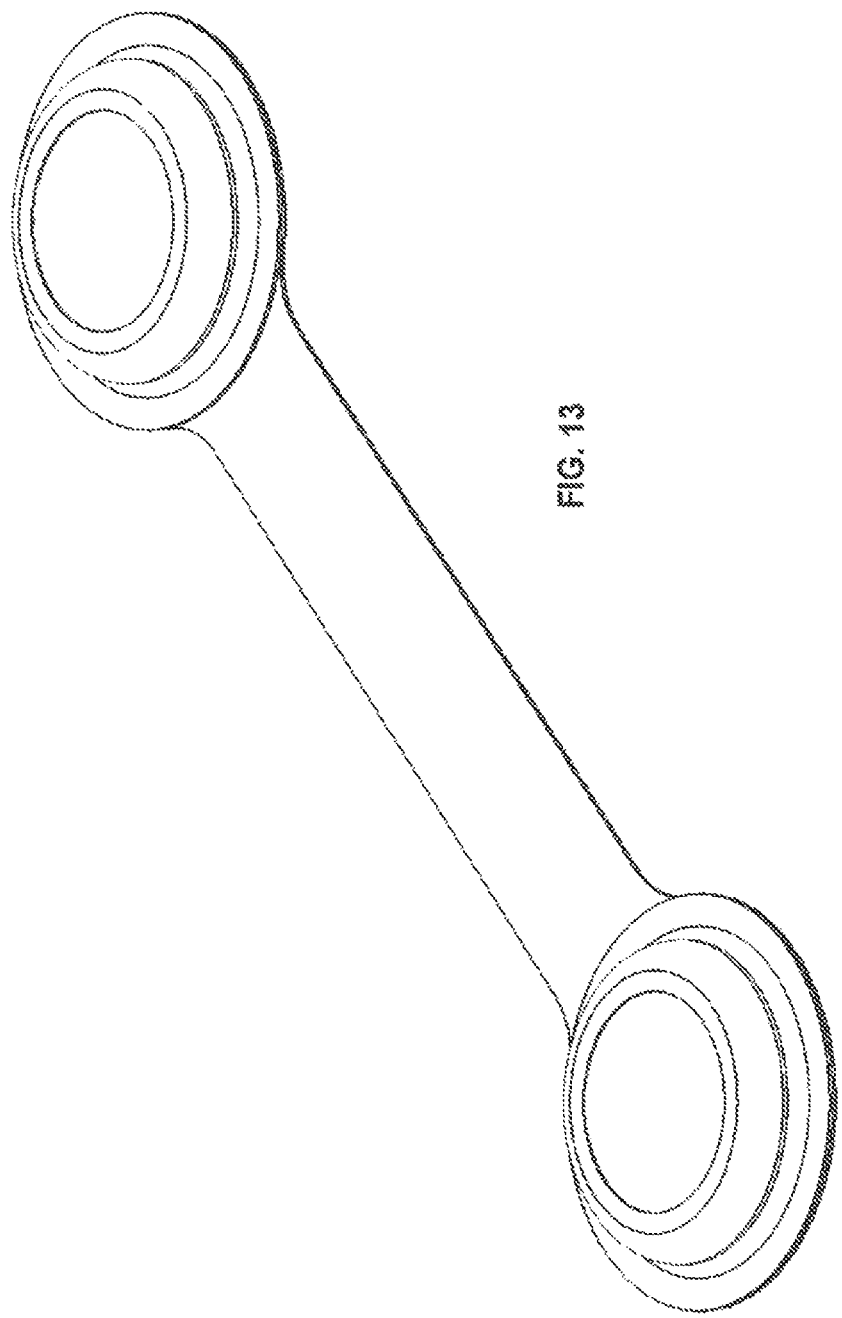
FIG. 13 is a diagram showing a front view of two exemplary ECG electrodes coupled to a sensor substrate plate according to one embodiment of the present invention.
Figure 17:
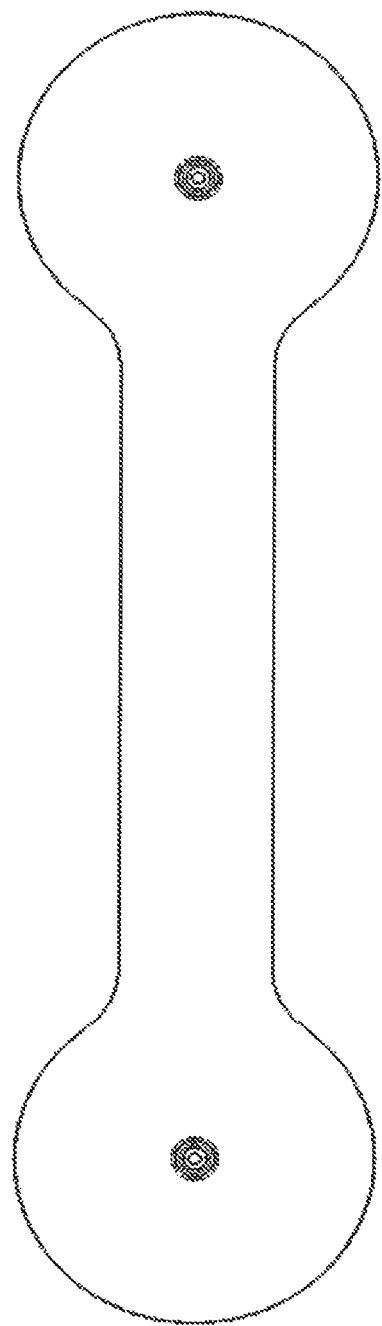
FIG. 17 is a diagram showing a top view of an exemplary sensor substrate plate according to one embodiment of the present invention.
Figure 18:
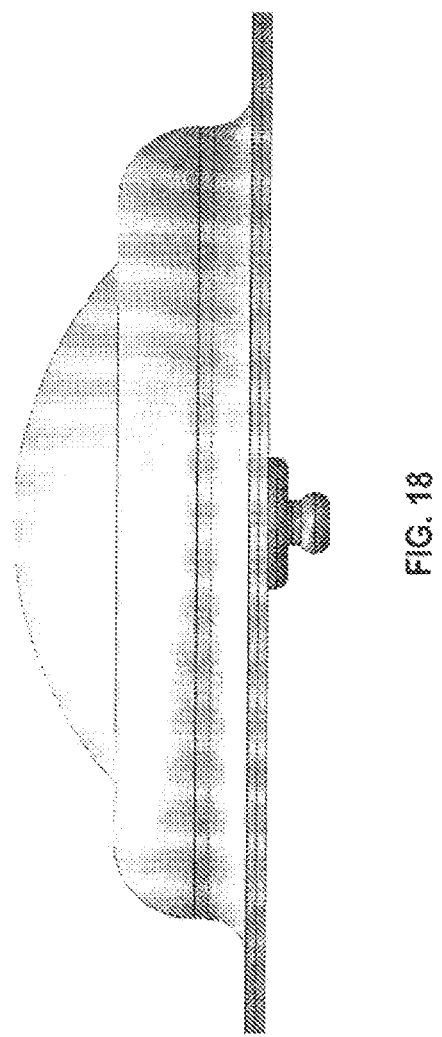
FIG. 18 is a diagram showing a side view of an exemplary ECG electrode coupled to a sensor substrate plate according to one embodiment of the present invention.
Figure 18:
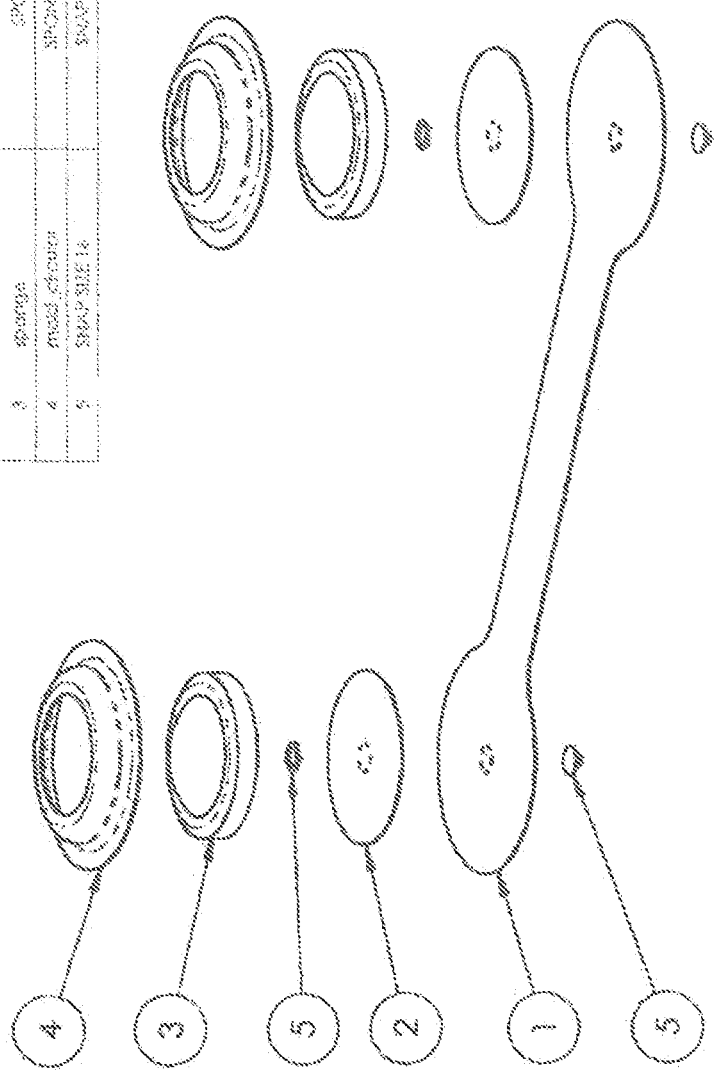
Figures 20, 21, 22:
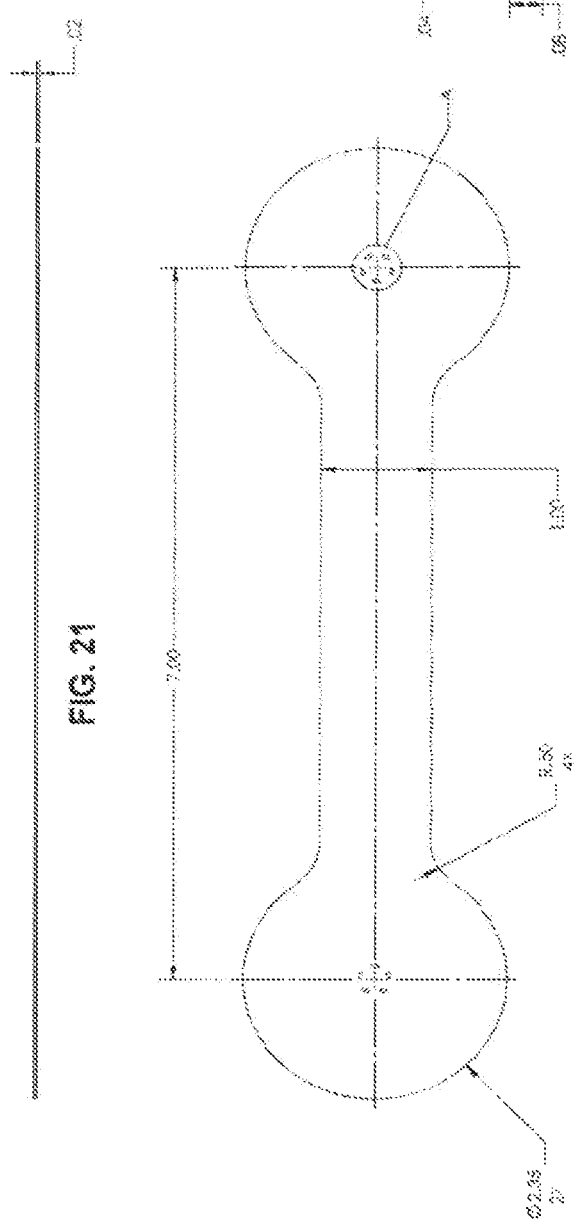
FIG. 20 is a diagram showing a top view of an exemplary sensor substrate plate according to one embodiment of the present invention.
FIG. 21 is a diagram showing a side view of an exemplary sensor substrate plate according to one embodiment of the present invention.
FIG. 22 is a diagram showing a top view of the through hole of an exemplary sensor substrate plate according to one embodiment of the present invention.
Figure 23:
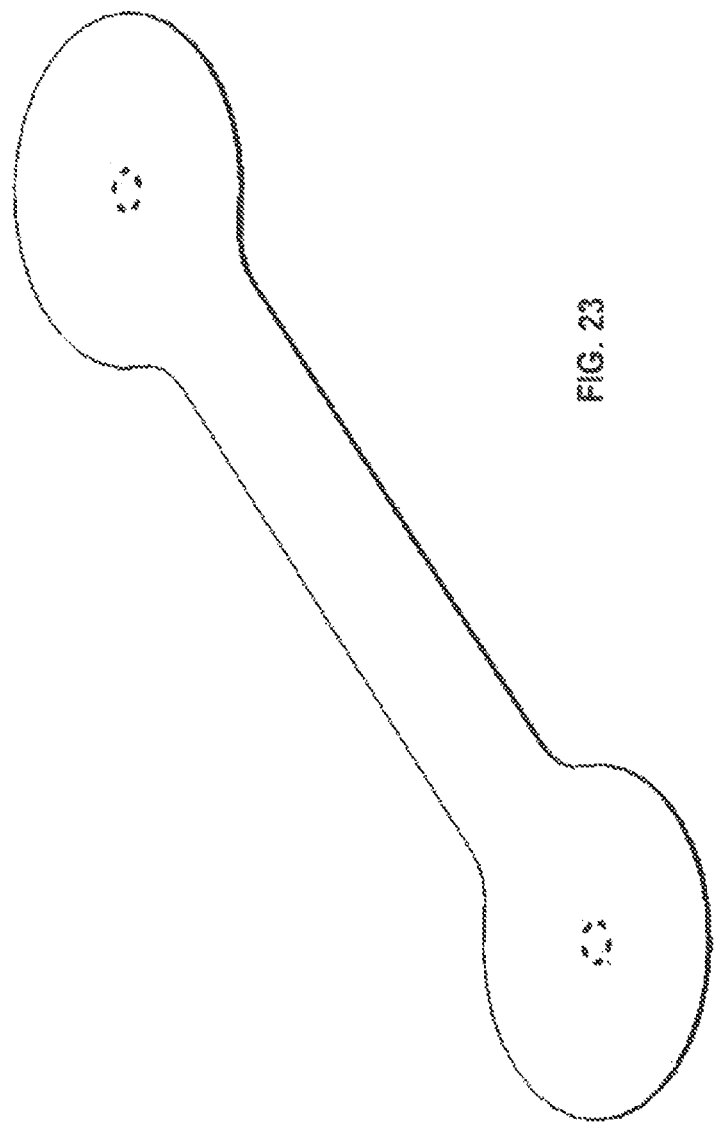
FIG. 23 is a diagram showing a top view of an exemplary sensor substrate plate according to one embodiment of the present invention.
Figure 30:
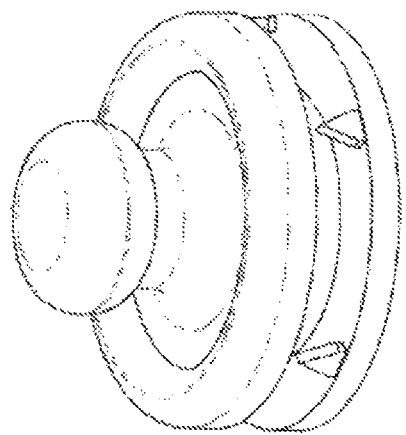
FIG. 30 is a diagram showing a side view of an exemplary fastener of the wet electrode according to one embodiment of the present invention.
Figure 31:
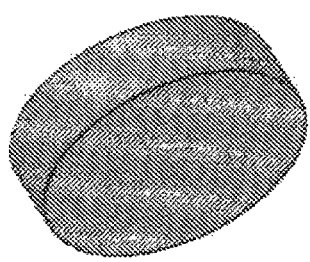
FIG. 31 is a diagram showing a side view of an exemplary main body of the wet electrode according to one embodiment of the present invention.
Figure 33:
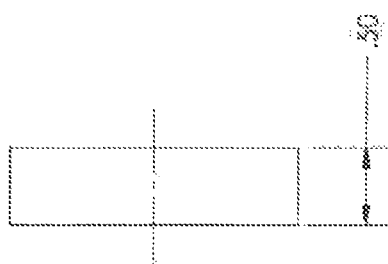
FIG. 33 is a diagram showing a side view of an exemplary main body of the wet electrode according to one embodiment of the present invention.
Figure 32:
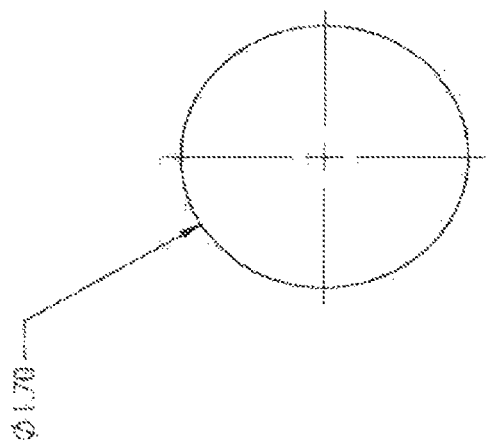
FIG. 32 is a diagram showing a top view of an exemplary main body of the wet electrode according to one embodiment of the present invention.
Figure 35:
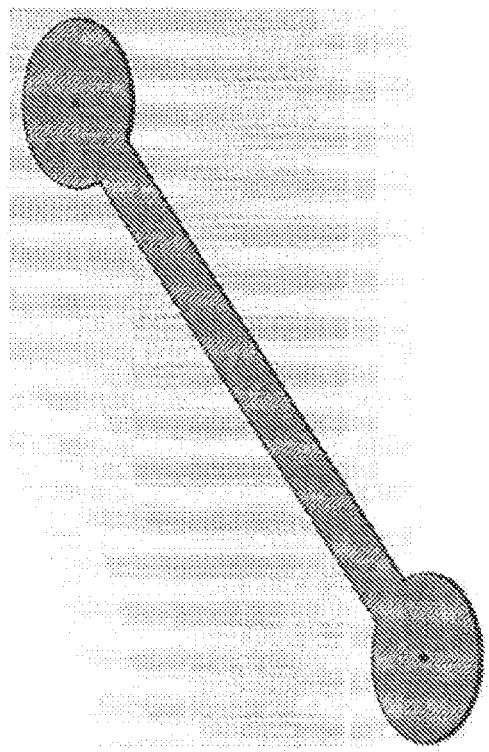
FIG. 35 is a diagram showing a top view of a sensor substrate plate according to one embodiment of the present invention.
Figure 34:
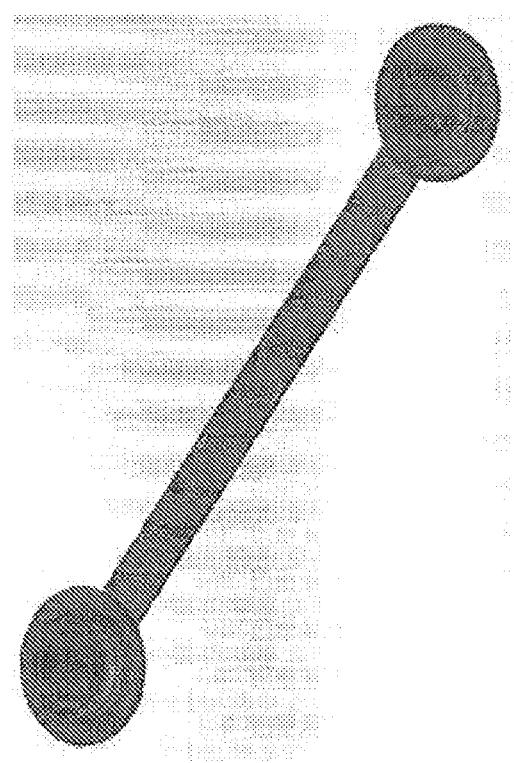
FIG. 34 is a diagram showing a top view of two exemplary ECG electrodes coupled to a sensor substrate plate according to one embodiment of the present invention.
Figure 36:
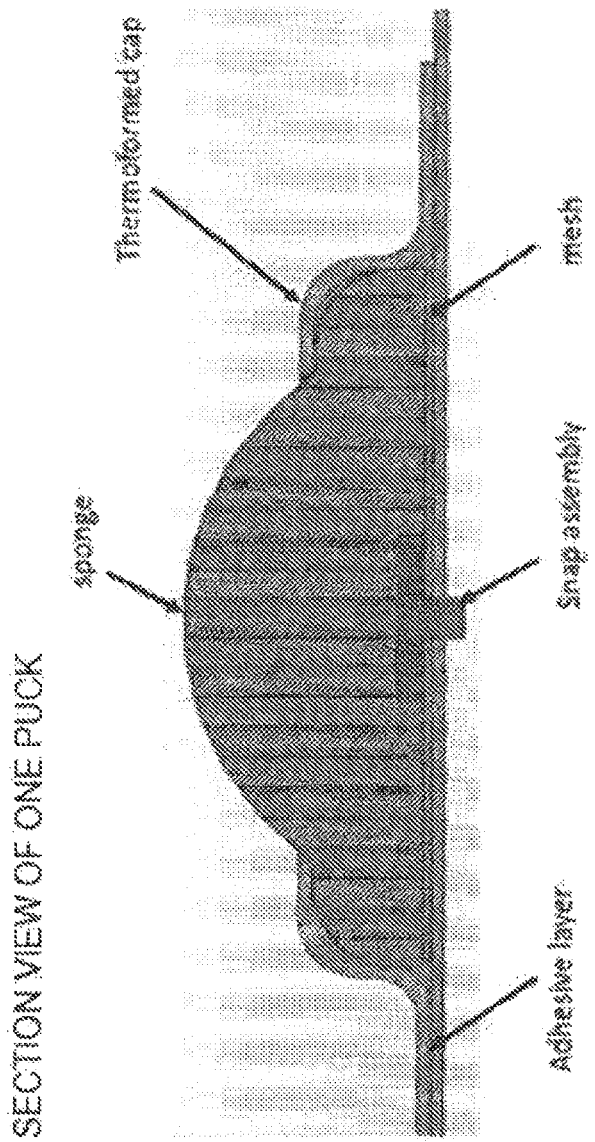
FIG. 36 is a diagram showing a side view of an exemplary ECG electrode coupled to a sensor substrate plate according to one embodiment of the present invention.
Figure 37:
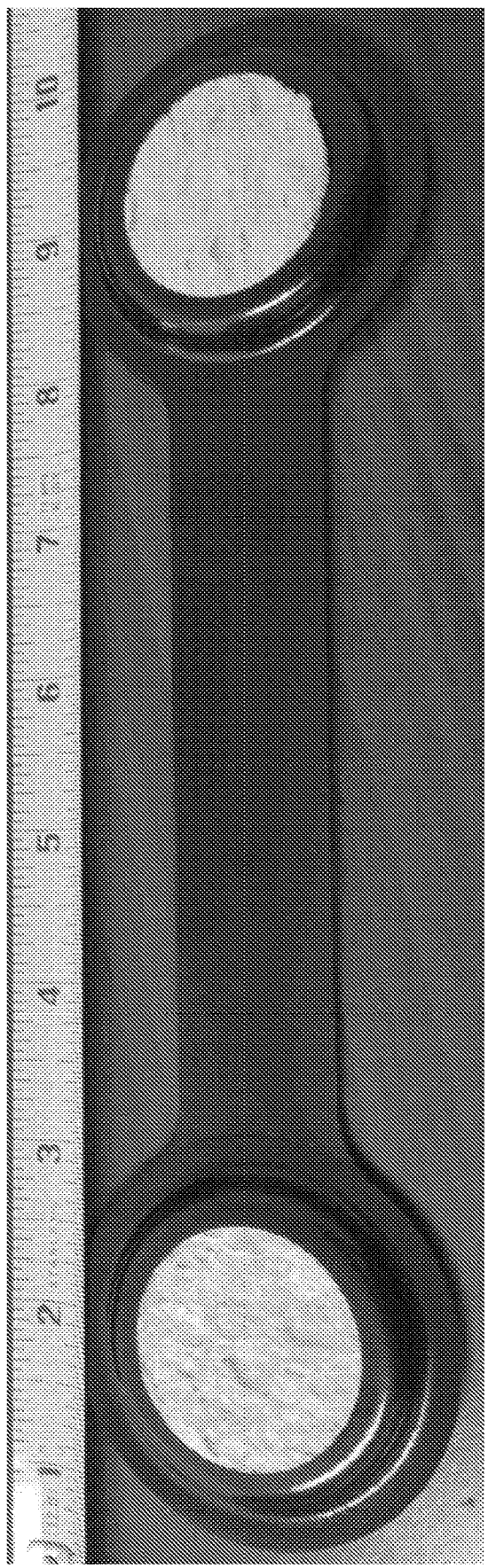
FIGS. 37 and 38 are Intentionally Omitted.
Figure 38:

In one embodiment, the first through hole 704 may be configured to hold a probe or a sensor for temperature and/or glucose measurement. As shown in FIG. 12B, the unused hole between the LED and the photo-detector and the first transducer is used for a temperature or a glucose probe/sensor.

Applicants envision that any shapes of the first end portion 707 and/or the second end portion 708 may be used for the sensor substrate plates of the present invention. For example, any shapes of the first end portion 707 and/or the second end portion 708 may be used when wet gel ECG electrodes with specific shape are used in combination with the sensor substrate plates. FIGS. 13-36 disclose specific examples of wet gel ECG electrodes coupled with the sensor substrate plates.

In one embodiment, the first end portion 707 and the second end portion 708 have shapes of circular plates and wherein the first end portion 707, the main body 701 and the second end portion 708 form an "S" shape of the sensor substrate plate 700.

Specifically, when the first end portion 707 and the second end portion 708 have shapes of circular plates, the second through hole 709 and/or the third through hole 710 may be located in the center of the circular plates. As such, the first wet electrode 58a and/or the second wet electrode 60a may be located in the center of the circular plates of the first end portion 707 and the second end portion 708. FIG. 7 shows an exemplary sensor substrate plate 700 where the first electrode and the second electrode are located in the center of the circular plates of the first end portion 707 and the second end portion 708.

In another aspect, the present invention discloses a device for monitoring vital signals of a patient. In one embodiment, the device includes the sensor substrate plate including all necessary electrode assemblies, sensor assemblies, LED and photo-detector assemblies, monitor assemblies and necessary power sources. In one embodiment, the necessary electrode assemblies include ECG electrodes such as wet gel ECG electrodes.

As discussed above, the device may be applicable to a non-human animal. In one embodiment, the device may be applicable to any patient selected from the group consisting of companion animals, primates, lab animals, pocket pets and reptiles. Although a dog is used as an exemplary patient, the present invention is applicable to any companion animals, any primates, any lab animals, any pocket pets or any reptiles.

In one embodiment, the means to removably hold the sensor substrate plate to the skin of a patient may include using a tape, a glue or adhesive, or any other removable attachment methods as appreciated by one skilled in the art.

In one embodiment, the means to removably hold the sensor substrate plate to the skin of a patient may be a vest or a harness.

As discussed above, the device may be orientated so that the first wet electrode 58a and/or the second wet electrode 60a may measure vital signs of two different tissues of a subject. For example, the first wet electrode 58a may be positioned to monitor the upper right chest of a dog patient and the second wet electrode 60a may be positioned to monitor the left leg axis of the dog patient's heart.

In one embodiment, the plurality of sensors or electrodes amounted to the slots of the upper surface of the senor substrate plate may include light sources such as LEDs and optical or photo-detectors.

In one embodiment, the device may include a first and a second LEDs mounted to an emitter assembly and a detector assembly spaced apart from and mounted substantially coplanar with respect to the emitter assembly for the monitoring and recording of pulse oximetry and non-invasive blood pressure.

In one embodiment, the device may also include ECG electrodes embedded on the sensor substrate plate or chassis for the recording of heart rate and ECG waveform and activity, respirations. Further, the device may also include temperature thermistors embedded on the sensor substrate plate or chassis for the monitoring of temperature. Provisions are also included to mount separate LED's and detector assemblies to non-invasively monitor blood glucose levels.

In one embodiment, the device may further comprise a power source, such as a battery.

In one embodiment, the device may be capable of monitoring biometric parameters comprising ECG, pulse oximetry, temperature glucose, respiration rate, blood pressure, a glucose level, a $SpO_2$ level, activity level, location and others.

In one embodiment, the at least one monitor comprises a monitor for Bluetooth transmission, displaying, recording, diagnosis or reporting.

In one embodiment, the majority of the device may be covered in a flap for protection with only the electrodes, light sources and photo-detectors exposed. In one embodiment, the flap may also include a through hole for a temperature or glucose probe/sensor. In another embodiment, the flap may not include any through hole for a temperature or glucose probe/sensor. As such, a temperature or glucose probe/sensor may also be covered by the flap.

In one embodiment, specific shaped electrodes or transducers may be used for the device of the present invention. For example, an "octopus" shape transducer as disclosed in U.S. Pat. No. 9,314,183 allows one to effectively measure vital signs of an animal subject without having to shave the area of the subject.

As shown in FIGS. 1A and 1B, only the "octopus" shape transducers, LEDs and photo-detectors are exposed and the majority surface of the device may be covered by a dark flap, which is held within a harness. Further, the dark flap may have an open end allowing the necessary wires or cables to pass through.

In another embodiment, a wet gel electrode may be used for the device of the present invention. For example, wet gel ECG electrodes with various shapes may be used in the present invention. FIGS. 13-36 include figures showing exemplary ECG electrodes coupled to the sensor substrate plates according to embodiments of the present invention. The specific shape of the ECG electrode is used as a non-limiting example. Applicants envision that any shape of wet get ECG electrode may be used in the present invention.

Although the present invention has been described in terms of one or more preferred embodiments, and it should be appreciated that many equivalents, alternatives, variations, and modifications, aside from those expressly stated, are possible and within the scope of the invention.

In one aspect, the present invention may also disclose an ECG electrode, such as a wet gel ECG electrode. FIGS. 13-36 include figures showing exemplary ECG electrodes according to embodiments of the present invention.

In one embodiment, the ECG electrode may be used in combination of the sensor substrate plate as discussed above.

In another embodiment, the ECG electrode may be used independently from any sensor substrate plate on a patient. For example, Applicants envision that a wet gel ECG electrode of the present invention may be used directly on a patient such as a non-human patient.

In one specific embodiment, the wet electrode may be directed and removably attached to the inside surface of a harness such as the one disclosed herein. For example, one or more wet electrodes may be coupled to the inner surface of the harness as shown in FIGS. 1-3.

In one specific example, one or more wet electrodes may be directed and may be removably attached to the inside surface of the harness as disclosed herein at suitable locations so that the main body of electrodes closely contact the skin of a subject, such as a dog. Because of the characteristic properties of the wet electrode, the subject does not need to remove hair before application of the wet electrode and the measurement.

Figures 39A, 39B:
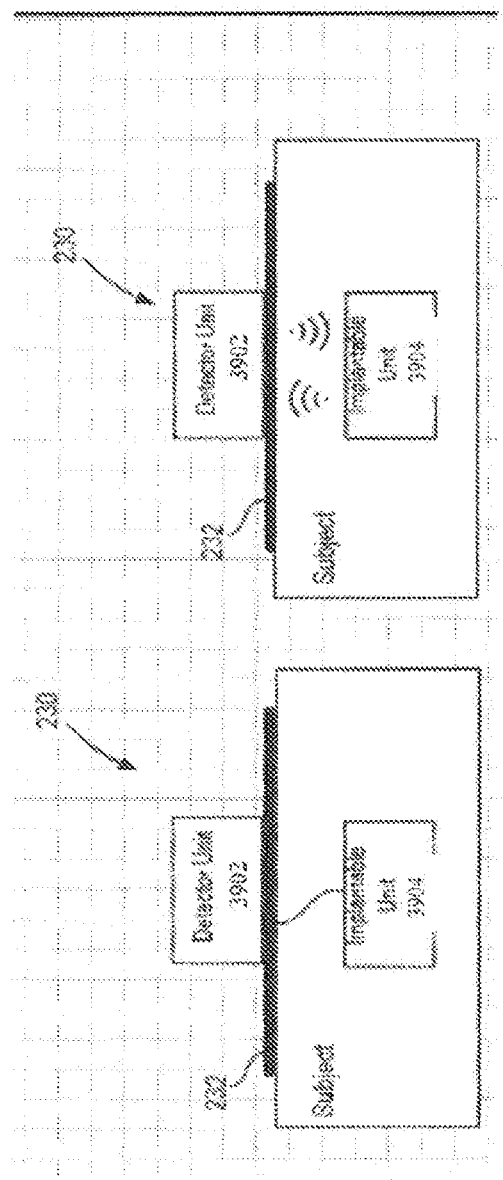
FIG. 39A and FIG. 39B are diagrams showing monitoring systems including implantable units applicable to the harness and the wet electrodes according to certain embodiments of the present invention.

FIG. 39A and FIG. 39B show embodiments of the monitoring system applicable to the harness and the sensor substrate. In particular, the figures illustrate an embodiment of a device 230 that may be used in a harness and/or a wet electrode, as described with reference to FIGS. 1-36. In general, the device 230 may include a detector unit 3902 and an implantable unit 3904. The implantable unit 3904 may be configured to detect various signals from the subject, as described. In addition, the implantable unit 3904 may also be configured to communicate detected signals using a wired as well as wireless connection, as shown. To this end, the detector unit 3902 and implantable unit 3904 may be configured with various hardware, including Bluetooth, WiFi or other wireless protocol.

The detector unit 3902 may be coupled to a substrate 232, which could be attached to the subject using a harness, as well as other wearable items or products, as described Signals received by the detector unit 3902 may be communicated to a monitoring unit, as described herein. The substrate 232 may be any of the sensor substrate plate as disclosed herein. In some implementations, the detector unit 3902 may advantageously amplify, filter, or otherwise preprocess the received signals detected by the implantable unit 3904.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

We claim:

1. A harness for use on an animal, the harness comprising:
   a bottom portion with a front edge, a rear edge, and a pocket;
   a top portion with a front edge, a rear edge, and an aperture;
   side portions extending from each side of the bottom portion;
   side portions extending from each side of the top portion; and
   mating connectors on the side portions allowing the side portions of the bottom portion to be connected to the side portions of the top portion,
   wherein a sensor is positioned within the pocket,
   wherein a first leg aperture and a second leg aperture for a front legs of the animal is formed when the side portions of the bottom portion and the side portions of the top portion are connected, and
   wherein the harness is configured to a size and a shape of the animal.

2. The harness of claim 1, wherein the matting connectors comprise a set of hooks located on the side portions of the bottom portion and a set of straps located on the side portions of the top portion whereby the set of straps insert and loop around the set of hooks.

* * * * *